(12) United States Patent
Bakus, II et al.

(10) Patent No.: US 10,843,997 B2
(45) Date of Patent: Nov. 24, 2020

(54) COMPOSITIONS FORMED FROM PLANT EXTRACTS AND METHODS OF PREPARATION THEREOF

(71) Applicant: APEEL TECHNOLOGY, INC., Goleta, CA (US)

(72) Inventors: Ronald C. Bakus, II, Santa Barbara, CA (US); Gabriel Rodriguez, Santa Barbara, CA (US); Camille Mol, Santa Barbara, CA (US); Louis Perez, Santa Barbara, CA (US)

(73) Assignee: APEEL TECHNOLOGY, INC., Goleta, CA (US)

( * ) Notice: Subject to any disclaimer, the term of this patent is extended or adjusted under 35 U.S.C. 154(b) by 0 days.

(21) Appl. No.: 16/414,735

(22) Filed: May 16, 2019

(65) Prior Publication Data
US 2019/0269145 A1    Sep. 5, 2019

Related U.S. Application Data

(63) Continuation of application No. PCT/US2017/062399, filed on Nov. 17, 2017.
(Continued)

(51) Int. Cl.
*C07C 67/03* (2006.01)
*C08J 11/16* (2006.01)
(Continued)

(52) U.S. Cl.
CPC ............... *C07C 67/03* (2013.01); *A23B 7/16* (2013.01); *A23B 9/14* (2013.01); *C08J 3/00* (2013.01); *C08J 11/16* (2013.01); *C11C 3/00* (2013.01); *A23V 2002/00* (2013.01); *C07C 67/02* (2013.01); *C08J 2367/02* (2013.01)

(58) Field of Classification Search
CPC . C07C 67/02; C07C 67/03; C08J 11/16; C08J 3/00
See application file for complete search history.

(56) References Cited

U.S. PATENT DOCUMENTS

| 1,016,761 A | 2/1912 | Moore |
| 1,943,468 A | 1/1934 | Bridgeman |

(Continued)

FOREIGN PATENT DOCUMENTS

| CN | 1208603 A | 2/1999 |
| CN | 1215420 A | 4/1999 |

(Continued)

OTHER PUBLICATIONS

Alvaro, et al., "Effects of peracetic acid disinfectant on the post-harvest of some fresh vegetables," Journal of Food Engineering, 95(1):11-15 (2009).
(Continued)

*Primary Examiner* — Yate' K Cutliff
(74) *Attorney, Agent, or Firm* — Haley Guiliano LLP; James F. Haley, Jr.; Brittany J. Barrett

(57) ABSTRACT

Embodiments described herein relate generally to plant extract compositions and methods to isolate fatty acid esters derived from crosslinked polyesters. Particular embodiments are directed to methods of preparing compositions of fatty acid esters by treating crosslinked polyesters or other crosslinked networks with an acid and an alcohol.

30 Claims, 30 Drawing Sheets

Related U.S. Application Data

(60) Provisional application No. 62/423,337, filed on Nov. 17, 2016.

(51) Int. Cl.
*A23B 7/16* (2006.01)
*A23B 9/14* (2006.01)
*C11C 3/00* (2006.01)
*C08J 3/00* (2006.01)
*C07C 67/02* (2006.01)

(56) References Cited

U.S. PATENT DOCUMENTS

| | | | |
|---|---|---|---|
| 2,213,557 A | 9/1940 | Tisdale |
| 2,222,000 A | 11/1940 | Schmidt |
| 2,275,659 A | 3/1942 | Steinle |
| 2,324,448 A | 7/1943 | Gottlieb |
| 2,333,887 A | 11/1943 | Redlinger |
| 2,342,063 A | 2/1944 | Sells |
| 2,657,282 A | 10/1953 | Te |
| 2,857,282 A | 10/1958 | Jansen |
| 3,189,467 A | 6/1965 | Kalmar |
| 3,232,765 A | 2/1966 | Rosenthal |
| 3,471,303 A | 10/1969 | Hamdy |
| 3,715,024 A | 2/1973 | Mumma |
| 3,997,674 A | 12/1976 | Ukai |
| 4,002,775 A | 1/1977 | Kabara |
| 4,421,775 A | 12/1983 | Chan, Jr. |
| 4,423,071 A | 12/1983 | Chignac |
| 4,654,370 A | 3/1987 | Marriott, III |
| 4,661,359 A | 4/1987 | Seaborne |
| 4,710,228 A | 12/1987 | Seaborne |
| 4,726,898 A | 2/1988 | Mills |
| 4,732,708 A * | 3/1988 | Ekman .................. C07C 51/09 554/138 |
| 4,820,533 A | 4/1989 | Seaborne |
| 4,874,618 A | 10/1989 | Seaborn |
| 4,960,600 A | 10/1990 | Kester |
| 4,962,885 A | 10/1990 | Coffee |
| 5,051,448 A | 9/1991 | Shashoua |
| 5,110,509 A | 5/1992 | Peter |
| 5,126,153 A | 6/1992 | Beck |
| 5,354,573 A | 10/1994 | Gross |
| 2,363,232 A | 11/1994 | Witt |
| 5,366,995 A | 11/1994 | Savage |
| 5,376,391 A | 12/1994 | Nisperos |
| 5,389,389 A | 2/1995 | Beck |
| 5,451,266 A | 9/1995 | Kirk |
| H1591 H | 9/1996 | Fulcher |
| 5,607,970 A | 3/1997 | Ishihara |
| 5,656,768 A | 8/1997 | Quinlan |
| 5,658,768 A | 8/1997 | Quinlan |
| 5,741,505 A | 4/1998 | Beyer |
| 5,827,553 A | 10/1998 | Dimitroglou |
| 5,832,527 A | 11/1998 | Kawaguchi |
| 5,906,831 A | 5/1999 | Larsson |
| 5,925,395 A | 7/1999 | Chen |
| 5,939,117 A | 8/1999 | Chen |
| 6,162,475 A | 12/2000 | Hagenmaier |
| 6,165,529 A | 12/2000 | Yang |
| 6,241,971 B1 | 6/2001 | Fox |
| 6,254,645 B1 | 7/2001 | Kellis, Jr. |
| 6,255,451 B1 | 7/2001 | Koch |
| 6,294,186 B1 | 9/2001 | Beerse |
| 6,348,217 B1 | 2/2002 | Santos |
| 6,503,492 B2 | 1/2003 | McGlone |
| 7,375,135 B2 | 5/2008 | Najib-Fruchart |
| 7,550,617 B2 | 6/2009 | Imig |
| 7,732,470 B2 | 6/2010 | Imig |
| 7,785,897 B2 | 8/2010 | Agnes |
| 7,851,002 B2 | 12/2010 | Hekal |
| 7,931,926 B2 | 4/2011 | Lidster |
| 7,943,336 B2 | 5/2011 | Viksoe-Nielsen |
| 8,101,221 B2 | 1/2012 | Chen |
| 8,119,178 B2 | 2/2012 | Lidster |
| 8,197,870 B2 | 6/2012 | Krasutsky |
| 8,247,609 B2 | 8/2012 | Rogues |
| 8,263,751 B2 | 9/2012 | Peterson |
| 8,424,243 B1 | 4/2013 | Narciso |
| 8,501,445 B2 | 8/2013 | Yoshikawa |
| 8,546,115 B2 | 10/2013 | Buchert |
| 8,586,807 B2 | 11/2013 | Hatcher |
| 8,609,169 B2 | 12/2013 | Chen |
| 8,752,328 B2 | 6/2014 | Kaiser |
| 8,846,355 B2 | 9/2014 | Yoshikawa |
| 9,095,152 B2 | 8/2015 | Munger |
| 9,102,125 B2 | 8/2015 | Battersby |
| 9,283,173 B2 | 3/2016 | Lederman |
| 9,284,432 B2 | 3/2016 | Yoshikawa |
| 9,475,643 B1 | 10/2016 | Odman |
| 9,714,399 B2 | 7/2017 | Verkuijl |
| 9,743,670 B2 | 8/2017 | Grund |
| 9,743,679 B2 | 8/2017 | Perez |
| 9,744,542 B2 | 8/2017 | Rogers |
| 9,770,041 B2 | 9/2017 | Dong |
| 9,957,215 B2 | 5/2018 | Perez |
| 1,009,201 A1 | 10/2018 | Holland |
| 1,026,670 A1 | 4/2019 | Perez |
| 1,040,737 A1 | 9/2019 | Bakus |
| 1,051,731 A1 | 12/2019 | Perez |
| 1,056,115 A1 | 2/2020 | Bakus |
| 2001/0042341 A1 | 11/2001 | Hamersky |
| 2002/0043577 A1 | 4/2002 | Krasutsky |
| 2003/0044488 A1 | 3/2003 | Roskam |
| 2003/0095141 A1 | 5/2003 | Shah |
| 2003/0109727 A1 | 6/2003 | Krasutsky |
| 2003/0124228 A1 | 7/2003 | Goto |
| 2003/0194445 A1 | 10/2003 | Kuhlner |
| 2004/0022906 A1 | 2/2004 | Petcavich |
| 2004/0120919 A1 | 6/2004 | Nguyen |
| 2004/0220283 A1 | 11/2004 | Zhang |
| 2005/0053593 A1 | 3/2005 | Wang |
| 2005/0233039 A1 | 10/2005 | Wolfe |
| 2005/0249856 A1 | 11/2005 | Marangoni |
| 2006/0037892 A1 | 2/2006 | Blanc |
| 2006/0057187 A1 | 3/2006 | Eskuchen |
| 2007/0278103 A1 | 12/2007 | Hoerr |
| 2008/0026120 A1 | 1/2008 | Petcavich |
| 2008/0038471 A1 | 2/2008 | Boger |
| 2008/0254987 A1 | 10/2008 | Liu |
| 2008/0262190 A1 | 10/2008 | Koskimies |
| 2008/0310991 A1 | 12/2008 | Webster |
| 2009/0042985 A1 | 2/2009 | Bhaggan |
| 2009/0104446 A1 | 4/2009 | Guillet |
| 2009/0123632 A1 | 5/2009 | Klemann |
| 2009/0142453 A1 | 6/2009 | Lobisser |
| 2009/0152371 A1 | 6/2009 | Stark |
| 2009/0325240 A1 | 12/2009 | Daniell |
| 2010/0029778 A1 | 2/2010 | Bailey |
| 2010/0104710 A2 | 4/2010 | Petcavich |
| 2010/0186674 A1 | 7/2010 | Cahill, Jr. |
| 2010/0210745 A1 | 8/2010 | McDaniel |
| 2010/0278784 A1 | 11/2010 | Pojasek |
| 2010/0292426 A1 | 11/2010 | Hossainy |
| 2010/0297273 A1 | 11/2010 | Lederman |
| 2011/0240064 A1 | 10/2011 | Wales |
| 2011/0244095 A1 | 10/2011 | Sardo |
| 2011/0280942 A1 | 11/2011 | Schad |
| 2012/0003356 A1 | 1/2012 | Ekanayake |
| 2012/0103790 A1 | 5/2012 | Krull |
| 2012/0251675 A1 | 10/2012 | Sowa |
| 2013/0095141 A1 | 4/2013 | Schad |
| 2013/0121648 A1 | 5/2013 | Hung |
| 2013/0209617 A1 | 8/2013 | Lobisser |
| 2013/0216488 A1 | 8/2013 | Hernandez-Brenes |
| 2013/0323378 A1 | 12/2013 | Stark |
| 2014/0033926 A1 | 2/2014 | Fassel |
| 2014/0199449 A1 | 7/2014 | Hernandez |
| 2014/0205722 A1 | 7/2014 | Quintanar |
| 2014/0221308 A1 | 8/2014 | Baker |
| 2014/0234921 A1 | 8/2014 | Nyyssola |
| 2014/0348945 A1 | 11/2014 | Dong |

(56) References Cited

U.S. PATENT DOCUMENTS

| | | | |
|---|---|---|---|
| 2015/0030780 A1* | 1/2015 | Rogers | A23B 4/10 427/483 |
| 2015/0079248 A1 | 3/2015 | Nussinovitch | |
| 2015/0210855 A1 | 7/2015 | Firth | |
| 2016/0002483 A1 | 1/2016 | Zhao | |
| 2016/0213030 A1 | 7/2016 | Schad | |
| 2016/0256429 A1 | 9/2016 | Spanova | |
| 2016/0324172 A1 | 11/2016 | Williams | |
| 2017/0049119 A1 | 2/2017 | Perez | |
| 2017/0073532 A1 | 3/2017 | Perez | |
| 2017/0318827 A1 | 11/2017 | Perez | |
| 2017/0320077 A1 | 11/2017 | Rogers | |
| 2017/0332650 A1 | 11/2017 | Holland | |
| 2018/0044276 A1 | 2/2018 | Perez | |
| 2018/0368426 A1 | 2/2018 | Holland | |
| 2018/0092811 A1 | 4/2018 | Klee | |
| 2018/0179401 A1 | 6/2018 | Perez | |
| 2018/0222835 A1 | 8/2018 | Bakus | |
| 2018/0258296 A1 | 9/2018 | Perez | |
| 2018/0317509 A1 | 11/2018 | Van Velzen | |
| 2018/0368427 A1 | 12/2018 | Rogers | |
| 2019/0031590 A1 | 1/2019 | Bakus | |
| 2019/0104748 A1 | 4/2019 | Kaun | |
| 2019/0269144 A1 | 9/2019 | Kaun | |
| 2020/0068912 A1 | 3/2020 | Hernandez | |
| 2020/0093147 A1 | 3/2020 | Perez | |
| 2020/0100514 A1 | 4/2020 | Bakus | |

FOREIGN PATENT DOCUMENTS

| | | |
|---|---|---|
| CN | 1616561 A | 5/2005 |
| CN | 101035926 A | 9/2007 |
| CN | 101356012 A | 1/2009 |
| CN | 102291986 A | 1/2010 |
| CN | 102335142 A | 2/2012 |
| CN | 103283830 A | 9/2013 |
| CN | 103719261 A | 4/2014 |
| DE | 2505428 A1 | 8/1976 |
| DE | 362219 A1 | 1/1988 |
| EP | 0104043 | 3/1984 |
| EP | 1020124 | 7/2000 |
| EP | 2389814 | 11/2011 |
| ES | 1041955 | 8/1999 |
| JP | 62126931 A | 6/1967 |
| JP | S541139645 A | 10/1979 |
| JP | S58034034 A | 2/1983 |
| JP | S63062574 A | 3/1988 |
| JP | H04507192 A | 12/1992 |
| JP | 2002531075 A | 9/2002 |
| JP | 2003522130 A | 7/2003 |
| JP | 2008504442 A | 2/2008 |
| JP | 2009527357 A | 7/2009 |
| JP | 2012515561 A | 7/2012 |
| WO | WO1993006735 | 4/1993 |
| WO | WO2001001980 | 1/2001 |
| WO | WO2004030455 | 4/2004 |
| WO | WO2009119730 | 10/2009 |
| WO | WO2011014831 | 2/2011 |
| WO | WO2012042404 | 4/2012 |
| WO | WO2014206911 | 12/2014 |
| WO | WO2015017450 | 2/2015 |
| WO | WO2015028299 | 3/2015 |
| WO | WO2015052433 | 4/2015 |
| WO | WO2015176020 | 11/2015 |
| WO | WO2016168319 | 10/2016 |
| WO | WO2016187581 | 11/2016 |
| WO | WO2017043972 | 3/2017 |
| WO | WO2017048951 | 3/2017 |
| WO | WO2017100636 | 6/2017 |
| WO | WO2017132281 | 8/2017 |
| WO | WO2017172951 | 10/2017 |
| WO | WO2018009846 | 1/2018 |
| WO | WO2018094269 | 5/2018 |

OTHER PUBLICATIONS

Alvira, et al., "Pretreatment Technologies for an Efficient Bioethanol Production Process Based on Enzymatic Hydrolysis: A Review," Bioresource Technology, 101(13):4851-4861 (2010).

Andrade, et al., "Atomizing Spray Systems for Application of Edible Coatings," Comprehensive Reviews in Food Science and Food Safety, 11(3):323-337 (2012).

Ayala-Zavala, et al., "High Relative Humidity In-Package of Fresh-Cut Fruits and Vegetables: Advantage or Disadvantage Considering Microbiological Problems and Antimicrobial Delivering Systems?" Journal of Food Science, 73:R41-R47 (2008).

Baker, et al., "Cutin Degradation by Plant Pathogenic Fungi," Physiology and Biochemistry, 68:1577-1584 (1978).

Banerjee, et al., "Electrospray Ionization Mass Spectrometry: A Technique to Access the Information Beyond the Molecular Weight of the Analyte," International Journal of Analytical Chemistry, Article ID 282574, 2012:10.1155/2012/282574, (2011) (40 pages).

Bateman, et al, "Supporting Information for Manuscript es-2008-01226w—The Effect of Solvent on the Analysis of Secondary Organic Aerosol Using Electrospray Ionization Mass Spectrometry," [online] 2008; available from the Internet URL: http://aerosol.chem.uci.edu/publications/Irvine/2008.sub.--Bateman.sub.--- EST.sub.--S0A.sub.--solvent.sub.--effects.sub.--supporting.sub.--info.pdf (6 pages).

Bateman, et al., "The Effect of Solvent on the Analysis of Secondary Organic Aerosol Using Electrospray Ionization Mass Spectrometry," Environmental Science & Technology, 42(19):7341-7346 (2008).

Ben-Yehoshua, et al., "Modified-atmosphere packaging of fruits and vegetables: reducing condensation of water in bell peppers and mangoes," Acta Horticulturae (ISHS), 464:387-392 (1998).

Bewick, et al., "Evaluation of Epicuticular Wax Removal from Whole Leaves with Chloroform," Weed Technology, 7(3):706-716 (1993).

Bourtoom, "Edible films and coatings: characteristics and properties," International Food Research Journal, 15(3):237-248 (2008).

Cantwell, "Properties and recommended conditions for long-term storage of fresh fruits and vegetables," Nov. 2001 (8 Pages).

Cech, et al., "Practical Implications of Some Recent Studies in Electrospray Ionization Fundamentals," Mass Spectrometry Reviews, 20:362-387 (2001).

Chen, et al., "Electrospraying of Conducting Liquids for Monodisperse Aerosol Generation in the 4 nm to 1.8 .mu.m Diameter Range," Journal of Aerosol Science, 26(6):963-977 (1995).

Cochran, "Solvation in supercritical water," Fluid Phase Equilibria, 71:1-16 (1992).

Deell, Jr, "Addition of sorbitol with KMnO4 improves broccoli quality retention in modified atmosphere packages", Journal of Food Quality, 29:65-75 (2006).

Dhall, "Advances in Edible Coatings for Fresh Fruits and Vegetables: A Review," Critical Reviews in Food Science and Nutrition, 53(5):435-450 (2013).

Duoren, "Green Plasticizers," Scientific and Technological Literature Publishing House, the 1st Edition, pp. 339-340 (Oct. 31, 2011) (English Translation).

Elgimabi, et al., "Effects of Bactericides and Sucrose-Pulsing on Vase Life of Rose Cut Flowers (Rosa hybirida)," Botany Research International, 2(3):164-168 (2009).

Enke, "A Predictive Model for Matrix and Analyte Effects in Electrospray Ionization of Singly-charged Ionic Analytes," Analytical Chemistry, 69(23):4885-4893 (1997).

Gabler, et al., "Impact of Postharvest Hot Water or Ethanol Treatment of Table Grapes on Gray Mold Incidence, Quality, and Ethanol Content," Plant Disease, 89(3):309-316 (2005).

Gaskell, "Principles and Practice," Journal of Mass Spectrometry, 32:677-688 (1997).

Gil, et al., "Fresh-cut product sanitation and wash water disinfection: Problems and solutions," International Journal of Food Microbiology, 134:37-45 (2009).

Graca, et al., "Glycerol and Glyceryl Esters of Omega-Hydroxyacids in Cutins," Phytochemistry, 61(2):205-215 (2002).

(56) References Cited

OTHER PUBLICATIONS

Graca, et al., "Linear and Branched Poly(omega-Hydroxyacid) Esters in Plant Cutins," Journal of Agricultural and Food Chemistry, 58(17):9666-9674 (2010).
Graca, "Suberin: the biopolyester at the frontier of plants," Oct. 2015, Frontiers in Chemistry, 3(62):1-11 (2015).
Hardenburg, et al., "The Commercial Storage of Fruits, Vegetables, and Florist and Nursery Stocks," United States Department of Agriculture, Agriculture Handbook, 66:6-7, 30, 50-51 (1986).
Hauff, et al., "Determination of hydroxylated fatty acids from the biopolymer of tomato cutin and their fate during incubation in soil," Phytochemical Analysis, Aug. 26, 2010, 21(6):582-589 (2010).
He, et al., "Stem end blockage in cut Grevillea 'Crimson Yul-lo' inflorescences," Postharvest Biology and Technology, 41:78-84 (2006).
Herrero, et al., "Compressed fluids for the extraction of bioactive compounds," TrAC Trends in Analytical Chemistry, 43(1):67-83 (2013).
Hojjati, et al., "Chemical Treatments of Eustoma Cut Flower Cultivars for Enhanced Vase Life," Journal of Agriculture and Social Sciences, 3(3):75-78 (2007).
Holcroft, "Water Relations in Harvested Fresh Produce," Pef White Paper No. 15-01, the Postharvest Education Foundation (Pef), 15 Pages (2015).
Huang, et al., "Automation of a Fourier Transform Ion Cyclotron Resonance Mass Spectrometer for Acquisition, Analysis, and E-mailing of High-resolution Exact-mass Electrospray Ionization Mass Spectral Data," Journal of American Society for Mass Spectrometry, 10:1166-1173 (1999).
Huang, et al., "Electron Transfer Reagent Anion Formation via Electrospray Ionization and Collision-induced Dissociation," Analytical Chemistry, 78(21):7387-7391 (2006).
Hudson, "Fatty Acids," Encyclopedia of Food Sciences and Nutrition (Second Edition), 2297-2300 (2003).
Javad, et al., "Effect of Cultivar on Water Relations and Postharvest Quality of Gethera (Gerbera jamesonii Bolus ex. Hook f.) Cut Flower," World Applied Sciences Journal, 18(5):698-703 (2012).
Javad, et al. "Postharvest evaluation of vase life, stem bending and screening of cultivars of cut gerbera (Getherajamesonii Bolux ex. Hook f.) flowers," African Journal of Biotechnology, 10(4):560-566 (2011).
Jaworek, "Electrospray Droplet Sources for Thin Film Deposition," Journal of Material Sciences, 42:266-297 (2007).
Jenkin, et al., "Isolation and Compositional Analysis of Plant Cuticle Lipid Polyester Monomers," Journal of Visualized Experiments, 105:e53386, 10 pages (2015).
Jerome, et al., ""One pot" and selective synthesis of monoglycerides over homogeneous and heterogeneous guanidine catalysts," Green Chemistry, 6:72-74 (2004).
Jiabin, "Rubberized Fabrics and Products Thereof," World Rubber Industry, 6:27-32 (2000) (English Translation-18 pages).
Jingmei, et al., "Preparation of Modified Starch/PLA Blends," New Chemical Materials, 39(6):125-129 (2011).
Jones, et al., "Pulsing with Triton X-100 Improves Hydration and Vase Life of Cut Sunflowers (*Helianthus annuus*L.)", HortScience, 28(12):1178-1179 (1993).
Karabulut, et al., "Postharvest ethanol and hot water treatments of table grapes to control gray mold", Postharvest Biology and Technology, 34:169-177 (2004).
Kebarle, "Special Feature: Commentary—A Brief Overview of the Present Status of the Mechanisms Involved in Electrospray Mass Spectrometry," Journal of Mass Spectrometry, 35:804-817 (2000).
Keller, et al., "Interferences and Contaminants Encountered in Modern Mass Spectrometry," Analytica Chimica Acta, 627:71-81 (2008).
Kolattukudy, "Biopolyester Membranes of Plants: Cutin and Suberin," Science, 208(4447):990-1000 (1980).
Kolattukudy, Cutin from Plants. Biopolymers Online, 3a, 2005 (40 pages).
Krammer, et al., "Hydrolysis of esters in subcritical and supercritical water," Journal of Supercritical Fluids, 16:189-206 (2000).
Kroll, et al., "Review: Chemistry of Secondary Organic Aerosol: Formation and Evolution of Low-volatility Organics in the Atmosphere," Atmospheric Environment, 42:3593-3624 (2008).
Kulkarni, et al., "Natural Polymers—A comprehensive review," International Journal of Research in Pharmaceutical and Biomedical Sciences, 3(4):1597-1613 (2012).
Li, et al., "Direct Quantification of Organic Acids in Aerosols by Desorption Electrospray Ionization Mass Spectrometry," Atmospheric Environment, 43:2717-2720 (2009).
Loppinet-Serani, et al., "Supercritical water for environmental technologies," Journal of Chemical Technology & Biotechnology, 85:583-589 (2010).
Matic, "The chemistry of Plant Cuticles: a study of cutin form Agave americana L.," Biochemical Journal, 63(1):168-176 (1956).
Mattson, et al., "Synthesis and properties of glycerides," Journal of Lipid Research, 3(3):281-296 (1962).
Morton, "The Relationship of Concentration and Germicidal Efficiency of Ethyl Alcohol," Annals of New York Academy of Sciences, 53(1):191-196 (1950).
Nizkorodov, S., et al., "Molecular Chemistry of Organic Aerosols through the Application of High Resolution Mass Spectrometry," Phys. Chem. Chem. Phys, 2011, vol. 13, pp. 3612-3629.
Oh, et al., "Antimicrobial activity of ethanol, glycerol monolaurate or lactic acid against Listeria monocytogenes," International Journal of Food Microbiology, 20:239-246 (1993).
Olmez, et al., "Potential alternative disinfection methods for organic fresh-cut industry for minimizing water consumption and environmental impact," LWT—Food Science and Technology, 42:686-693 (2009).
Osman, et al., "Preparation, Isolation, and Characterization of Cutin Monomers and oligomers from Tomato Peels," Journal of Agricultural and Food Chemistry, 47(2):799 - 802 (1999).
Roy, et al., "Modified atmosphere and modified humidity packaging of fresh mushrooms," Journal of Food Science, 61:391-397 (1996).
Rujun, et al., "Surface Modification and Physical Properties of Inorganic Nanomaterials," Hefei University of Technology Press, 1st Edition, pp. 43-45 (2009).
Rutala, W. et al. "Guideline for Disinfection and Sterilization in Healthcare Facilities, 2008" CDC, 2008, 158 Pages.
Sasaki, et al., "Cellulose hydrolysis in subcritical and supercritical water", Journal of Supercritical Fluids, 13:261-268 (1998).
Sasaki, et al., "Dissolution and Hydrolysis of Cellulose in Subcritical and Supercritical Water," Industrial & Engineering Chemistry Research, 39:2883-2890 (2000).
Savage, "Organic Chemical Reactions in Supercritical Water," Chemical Reviews, 99:603621 (1999).
Schreiber, "Transport barriers made of cutin, suberin and associated waxes," Trends in Plant Science, 15(10):546-553 (2010).
Schweizer, et al. "Perception of free cutin monomers by plant cells," the Plant Journal, 10(2):331-341 (1996).
Schweizer, et al., "Plant Protection by Free Cutin Monomers in Two Cereal Pathosystems", Advances in Molecular Genetics of Plant-Microbe Interactions, 371-374 (1994) https://doi.org/10.1007/978-94-011-0177-6_55.
Shirazi, et al., "Controlling relative humidity in modified atmosphere packages of tomato fruit," HortScience, 27:336-339 (1992).
Steuter et al. "Water Potential of Aqueous Polyethylene Glycol," Plant Physiology, 67:64-67 (1981).
Takats, et al., "Special Feature: Perspective—Ambient Mass Spectrometry Using Desorption Electrospray Ionization (DES!): Instrumentation, Mechanisms and Applications in Forensics, Chemistry, and Biology," Journal of Mass Spectrometry, 40:1261-1275 (2005).
Tanaka, et al., "Quantitative Determination of Isomeric Glycerides, Free Fatty Acids and Triglycerides by Thin Layer Chromatography-Flame Ionization Detector System," Lipids, 15(10):872-875 (1980).
Technical Evaluation Report, "Glycerides (mono and di) Handling/Processing Compiled by OMRI for the USDA National Organic Program," Published Jan. 27, 2015, pp. 1-15.
Tegelaar, "Some mechanisms of flash pyrolysis of naturally occurring higher plant polyesters," Journal of Analytical and Applied Pyrolysis, 15, 2 pages. (1989) (Abstract).

(56) References Cited

OTHER PUBLICATIONS

Van Doorn, et al., "Alkylethoxylate surfactants for rehydration of roses and Bouvardia flowers," Postharvest Biology and Technology, 24:327-333 (2002).

Van Doorn, et al., "Effects of surfactants on the longevity of dry-stored cut flowering stems of rose, Bouvardia, and Astilbe," Postharvest Biology and Technology, 3:69-76 (1993).

Van Meeteren, "Water Relations and Keeping-Quality of Cut Gerbera Flowers. I. The Cause of Stem Break," Scientia Horticulturae, 8:65-74 (1978).

Wang, et al., "Evolution of the Solvent Polarity in an Electrospray Plume," Journal of the American Society for Mass Spectrometry, 21:378-385 (2010).

Weingartner, et al., "Supercritical water as a solvent", Angewandte Chemie, 44(18):2672-2692 (2005).

Wikipedia, "Paint-Wikipedia", https://en.wikipedia.org/w/index.php?title=Paint&oldid=563291624, Jul. 2013 (7 Pages).

Xizhong, et al., "Spray drying," the 2nd edition, Chemical Industry Press, pp. 147-151 (2003).

Yang, et al., "Progress on Graft Polymerization of Cellulose," Journal of Cellulose Science and Technology, 17(3) 6 pages (2009) (English Abstract Translation).

Yeats, et al., "The identification of cutin synthase formation of the plant polyester cutin,"Nature Chemical Biology, 8(7):609-611 (2012).

Zhu, et al., "Formation and Decompositions of Chloride Adduct Ions, [M + Cl], in Negative Ion Electrospray Ionization Mass Spectrometry," Journal of the American Society for Mass Spectrometry, 11:932-941 (2000).

Zhu, et al., "Ranking of a Gas-phase Acidities and Chloride Affinities of Monosaccharides and Linkage Specificity in Collision-induced Decompositions of Negative Ion Electrospray-generated Chloride Adducts of Oligosaccharides," Journal of the American Society for Mass Spectrometry, 12:1193-1204 (2001).

\* cited by examiner

| Eq. H$_2$SO$_4$ | Time (hrs.) | Temp (°C) | Crude Isolate (g) | Mass of Purified EtDHPA (g) |
|---|---|---|---|---|
| 2 | 48 | Reflux | 2.89 g [Avg.] ± 0.31 (n=3) (28.6%) | 0.81 g [Avg.] ± 0.035 (n=3) (8.1% overall) |
| 1 | 48 | Reflux | 2.14 g [Avg.] ± 0.44 (n=3) (21.4%) | 0.58 (5.8% overall) |
| 0.5 | 48 | Reflux | 1.58 (15.8%) | 0.32 (3.2% overall) |
| 0.25 | 48 | Reflux | 0.26 (2.6%) | NA |
| 0.1 | 48 | Reflux | Negligible | NA |
| 1 | 48 | 100 | 3.49 (35.0%) | 0.92 (9.2% overall) |
| 1 | 48 | 120 | 4.45 (44.4%) | 1.40 (14.0% overall) |
| 1 | 24 | 120 | 4.09 (40.7%) | 1.00 (10.0% overall) |
| 2 | 48 | 120 | 4.99 (49.6%) | 1.13 (11.3% overall) |
| 0.5 | 48 | 120 | 4.14 (41.2%) | 1.19 (11.9% overall) |
| 0.5 | 24 | 120 | 2.80 (27.9%) | 0.64 (6.4% overall) |
| 0.25 | 48 | 120 | 1.01 (10.1%) | 0.00 (0.00%) |

FIG. 5

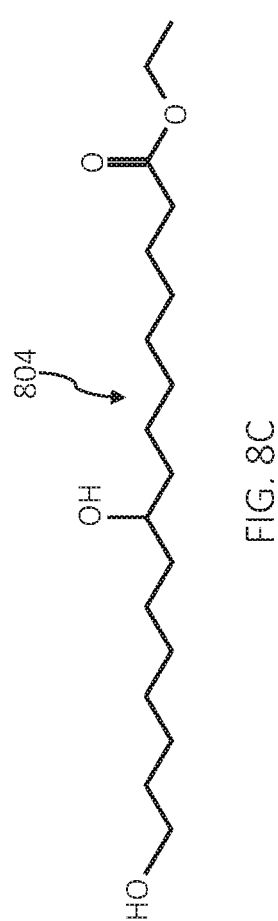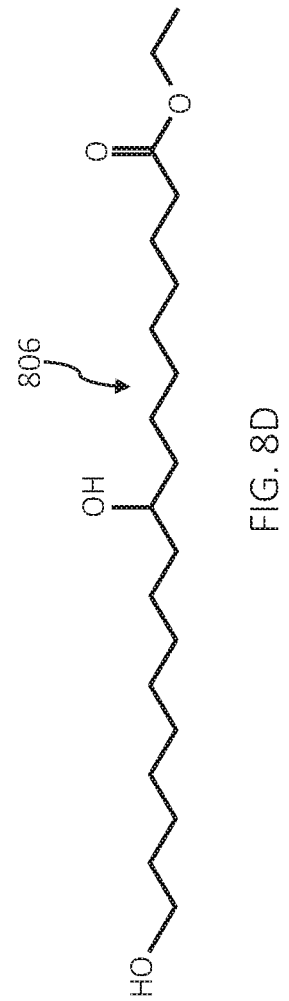

Palmitic acid derived:

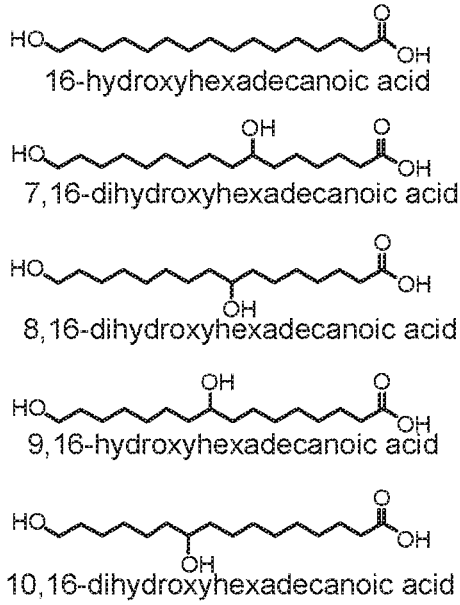

16-hydroxyhexadecanoic acid 7,16-dihydroxyhexadecanoic acid 8,16-dihydroxyhexadecanoic acid 9,16-hydroxyhexadecanoic acid 10,16-dihydroxyhexadecanoic acid Palmitoleic acid derived:

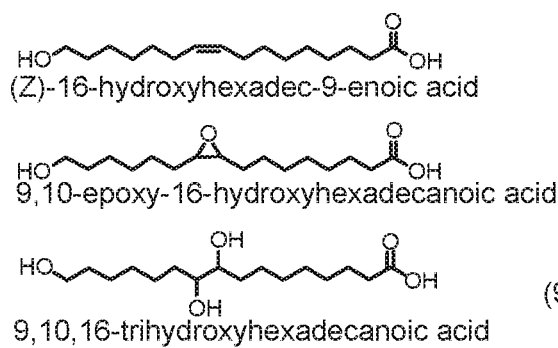

(Z)-16-hydroxyhexadec-9-enoic acid 9,10-epoxy-16-hydroxyhexadecanoic acid 9,10,16-trihydroxyhexadecanoic acid Steric acid derived:

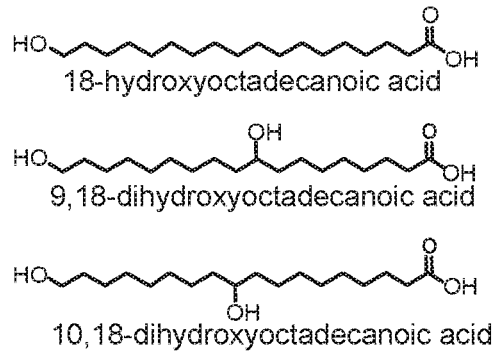

18-hydroxyoctadecanoic acid 9,18-dihydroxyoctadecanoic acid 10,18-dihydroxyoctadecanoic acid Oleic acid derived:

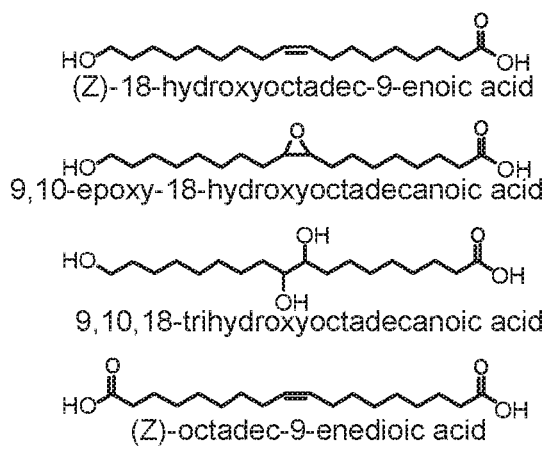

(Z)-18-hydroxyoctadec-9-enoic acid 9,10-epoxy-18-hydroxyoctadecanoic acid 9,10,18-trihydroxyoctadecanoic acid (Z)-octadec-9-enedioic acid Linoleic acid derived:

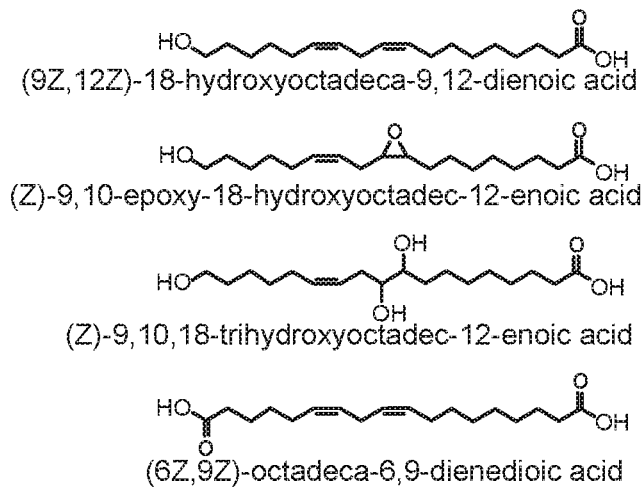

(9Z,12Z)-18-hydroxyoctadeca-9,12-dienoic acid (Z)-9,10-epoxy-18-hydroxyoctadec-12-enoic acid (Z)-9,10,18-trihydroxyoctadec-12-enoic acid (6Z,9Z)-octadeca-6,9-dienedioic acid

FIG. 14

COMPOSITIONS FORMED FROM PLANT EXTRACTS AND METHODS OF PREPARATION THEREOF

CROSS REFERENCE TO RELATED APPLICATIONS

This application is a continuation of International Application No. PCT/US2017/062399, filed Nov. 17, 2017, which claims priority to and the benefit of U.S. Provisional Patent No. 62/423,337, filed Nov. 17, 2016, the contents of which are hereby incorporated by reference in their entirety.

FIELD OF THE DISCLOSURE

The present disclosure relates to compositions formed from plant extracts, and to methods of forming the same.

BACKGROUND

Common agricultural products are susceptible to degradation and decomposition (i.e., spoilage) when exposed to the environment. Such agricultural products can include, for example, eggs, fruits, vegetables, produce, seeds, nuts, flowers, and/or whole plants (including their processed and semi-processed forms). Non-agricultural products (e.g., vitamins, candy, etc.) are also vulnerable to degradation when exposed to the ambient environment. The degradation of the agricultural products can occur via abiotic means as a result of evaporative moisture loss from an external surface of the agricultural products to the atmosphere and/or oxidation by oxygen that diffuses into the agricultural products from the environment and/or mechanical damage to the surface and/or light-induced degradation (i.e., photodegradation). Furthermore, biotic stressors such as, for example, bacteria, fungi, viruses, and/or pests can also infest and decompose the agricultural products.

Conventional approaches to preventing degradation, maintaining quality, and increasing the life of agricultural products include refrigeration and/or special packaging. Refrigeration requires capital-intensive equipment, demands constant energy expenditure, can cause damage or quality loss to the product if not carefully controlled, must be actively managed, and its benefits are lost upon interruption of a temperature-controlled supply chain. Special packaging can also require expensive equipment, consume packaging material, increase transportation costs, and require active management. Despite the benefits that can be afforded by refrigeration and special packaging, the handling and transportation of the agricultural products can cause surface abrasion or bruising that is aesthetically displeasing to the consumer and serves as points of ingress for bacteria and fungi. Moreover, the expenses associated with such approaches can add to the cost of the agricultural product.

The cells that form the aerial surface of most plants (such as higher plants) include an outer envelope or cuticle, which provides varying degrees of protection against water loss, oxidation, mechanical damage, photodegradation, and/or biotic stressors, depending upon the plant species and the plant organ (e.g., fruit, seeds, bark, flowers, leaves, stems, etc.). Cutin, which is a biopolyester derived from cellular lipids, forms the major structural component of the cuticle and serves to provide protection to the plant against environmental stressors (both abiotic and biotic). The thickness, density, as well as the composition of the cutin (i.e., the different types of monomers that form the cutin and their relative proportions) can vary by plant species, by plant organ within the same or different plant species, and by stage of plant maturity. The cutin-containing portion of the plant can also contain additional compounds (e.g., epicuticular waxes, phenolics, antioxidants, colored compounds, proteins, polysaccharides, etc.). This variation in the cutin composition as well as the thickness and density of the cutin layer between plant species and/or plant organs and/or a given plant at different stages of maturation can lead to varying degrees of resistance between plant species or plant organs to attack by environmental stressors (i.e., water loss, oxidation, mechanical injury, and light) and/or biotic stressors (e.g., fungi, bacteria, viruses, insects, etc.).

SUMMARY

Embodiments described herein relate generally to plant extract compositions and methods to isolate cutin-derived monomers, oligomers, and/or their esters, and mixtures thereof, in particular for applications in agricultural coating formulations. Particular embodiments are directed to methods of preparing compositions of fatty acid esters by treating crosslinked polyesters or other crosslinked networks with an acid and an alcohol.

In a first aspect, a method of preparing a composition comprising fatty acid esters includes providing a crosslinked polyester comprising fatty acids, treating the crosslinked polyester with an acid and an alcohol, and removing the acid and the alcohol to isolate the resulting fatty acid esters.

In a second aspect, a method of preparing a composition comprising esters includes providing a crosslinked network including hydrolyzable or transesterifiable bonds, treating the crosslinked network with an acid and an alcohol, and removing the acid and the alcohol to isolate the resulting esters.

In a third aspect, a method of preparing a composition comprising cutin-derived monomers, oligomers, esters, or combinations thereof includes providing cutin obtained from plant matter, and treating the cutin with a solvent, thereby causing the cutin to decompose into the cutin-derived monomers, oligomers, esters, or combinations thereof. The method further includes removing the solvent to isolate the cutin-derived monomers, oligomers, esters, or combinations thereof. The resulting composition is characterized as being in the form of a solid powder with little or no coloration.

In a fourth aspect, a method of forming a protective coating on a substrate includes obtaining fatty acid esters, wherein the obtaining of the fatty acid esters comprises treating a crosslinked polyester comprising fatty acids with an acid and an alcohol, and removing the acid and alcohol to isolate the resulting fatty acid esters. The method further includes causing the fatty acid esters to be applied to a surface of the substrate to form the protective coating.

In a fifth aspect, a method of preparing a composition comprising cutin-derived monomers, oligomers, esters, or combinations thereof from cutin-containing plant matter includes obtaining cutin from the cutin-containing plant matter and adding the cutin to a solvent comprising an acid and an alcohol to form a first mixture. The method further includes removing the solvent to isolate the cutin-derived monomers, oligomers, esters, or combinations thereof. The resulting cutin-derived monomers, oligomers, esters, or combinations thereof can comprise one or more compounds of Formula I:

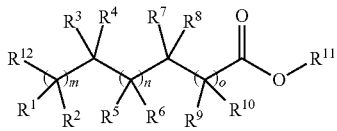

(Formula I)

wherein $R^1$, $R^2$, $R^3$, $R^4$, $R^5$, $R^6$, $R^7$, $R^8$, $R^9$, $R^{10}$, $R^{11}$, $R^{12}$, m, n, and o are as described below.

Methods and formulations described herein can each include one or more of the following steps or features, either alone or in combination with one another. The crosslinked polyester or crosslinked network can be naturally occurring. The crosslinked polyester or crosslinked network can be derived from plant matter. The crosslinked polyester or crosslinked network can be cutin. The cutin can be derived from plant skins. Treating the crosslinked polyester or crosslinked network with the acid and the alcohol can include suspending or dissolving the crosslinked polyester or crosslinked network and the acid in the alcohol to form a solution. The acid can be a strong acid. A concentration of the acid in the solution can be greater than 100 µmol/L. The solution can further comprise a non-reactive secondary solvent.

The crosslinked polyester or crosslinked network can contain endogenous water. Treating the crosslinked polyester with the acid and the alcohol can further comprise heating the crosslinked polyester, the acid, and the alcohol. Heating the crosslinked polyester, the acid, and the alcohol can comprise refluxing the polyester, the acid, and the alcohol at the boiling point of the alcohol. The polyester, the acid, and the alcohol can be heated in a sealed vessel above the boiling point of the alcohol. The alcohol can comprise ethanol, methanol, propanol, glycerol, isopropanol, or combinations thereof. The alcohol can be a primary or secondary alcohol. Removing the acid can comprise neutralizing the acid. Removing the alcohol can comprise evaporating the alcohol.

The acid can be sulfuric acid, triflic acid, hydrochloric acid, hydrobromic acid, hydroiodic acid, para-toluenesulfonic acid, or a combination thereof. The acid can be catalytic. The acid can be utilized in superstoichiometric amounts. A molar ratio of the alcohol to the fatty acids can be greater than 1. The fatty acids of the crosslinked polymer or crosslinked network can comprise 16-hydroxy hexadecanoic acid, 9,16-dihydroxyhexadecanoic acid, 10,16-dihydroxyhexadecanoic acid, 18-hydroxysteric acid, 18-hydroxy-(9Z)-octadec-9-enoic acid, 9,10-epoxy-18-hydroxy octadecanoic acid, 9,10,18-trihydroxyoctadecanoic acid, or a combination thereof. The resulting fatty acid esters can comprise ethyl 16-hydroxyhexadecanoate, ethyl 9,16-dihydroxyhexadecanoate, ethyl 10,16-dihydroxyhexadecanoate, ethyl 18-hydroxyoctadecanoate, ethyl 18-hydroxy-(9Z)-octadec-9-enoate, ethyl 9,10-epoxy-18-hydroxyoctadecanoate, ethyl 9,10,18-trihydroxyoctadecanoate, or a combination thereof.

The method can be characterized as only requiring a single step to obtain the resulting fatty acid esters from the crosslinked polyester or crosslinked network. The fatty acid esters formed by any of the methods described herein can be applied to the surface of a substrate to form a protective coating. The substrate can be an edible substrate. The substrate can be a piece of produce. The substrate can be plant matter.

BRIEF DESCRIPTION OF THE FIGURES

FIGS. 5 and 6 illustrate results obtained from preparing a composition according to the method of FIG. 3.

FIGS. 8A, 8B, 8C, 8D, 8E, 8F, 8G, and 8H show the chemical structure of ethyl 10,16-dihydroxyhexadecanoate, ethyl 10,18-dihydroxyoctadecanoate, ethyl 9,16-dihydroxyhexadecanoate, ethyl 9,18-dihydroxyoctadecanoate, ethyl 9,10,16-trihydroxyhexadecanoate, ethyl 9,10,18-trihydroxyoctadecanoate, ethyl 9,10-epoxy-16-hydroxyhexadecanoate, and ethyl 9,10-epoxy-18-hydroxyoctadecanoic, respectively.

FIG. 14 depicts various cutin-derived monomers which may be obtained from the methods described herein and/or which may be treated according to the methods described herein for the purpose of coating and/or preserving fruits and vegetables.

Like reference symbols in the various drawings indicate like elements.

DETAILED DESCRIPTION

Figure 1:
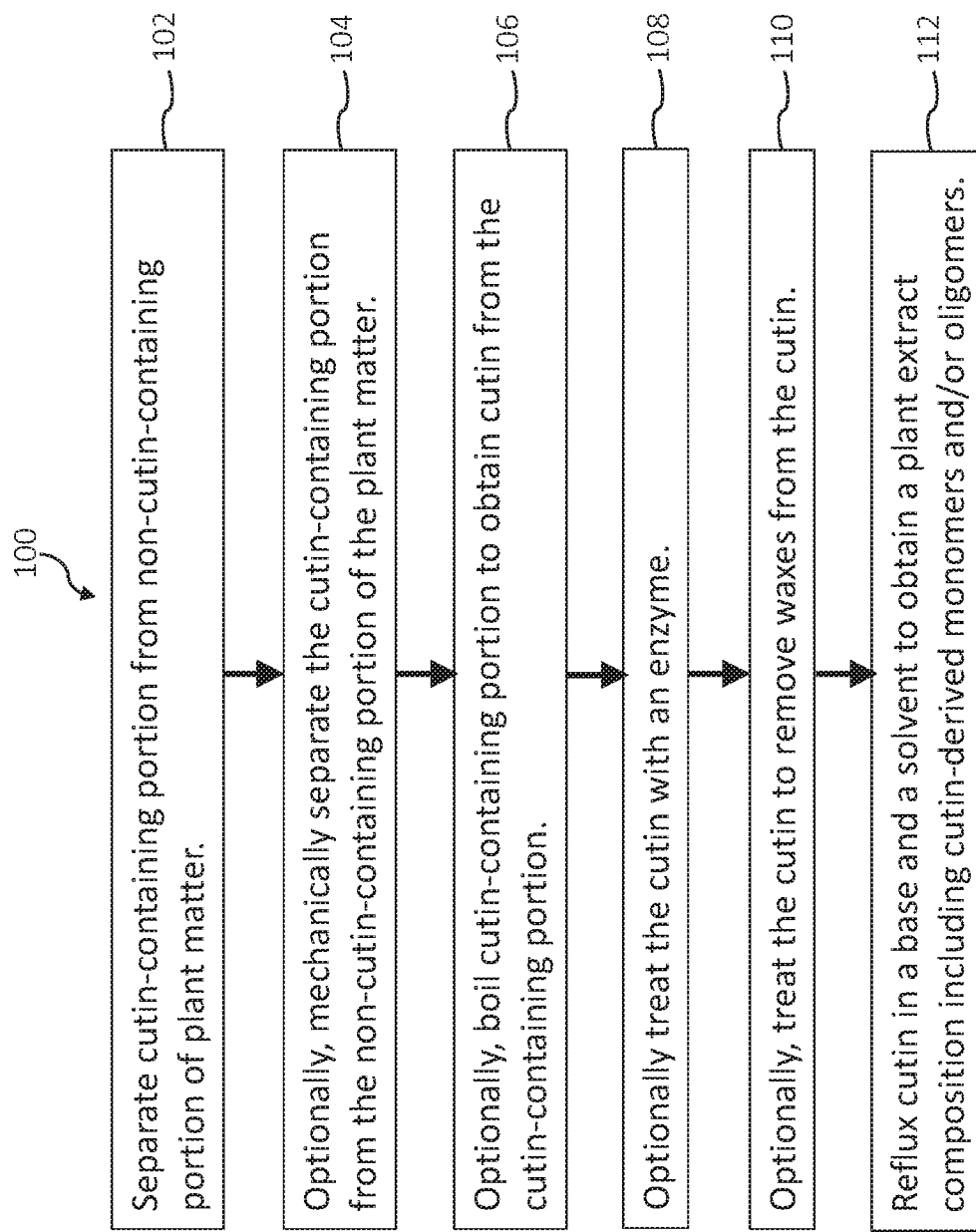
FIG. 1 is a schematic flow diagram of a first exemplary method for preparing a composition.

The biopolyester cutin forms the main structural component of the cuticle that composes the aerial surface of most land plants and plays a significant role in providing plants a protective barrier against both abiotic and biotic stressors. The thickness, density, as well as the composition of the cutin (i.e., the different types of monomers that form the cutin and their relative proportions) can vary by plant species, by plant organ within the same or different plant species, and by stage of plant maturity. These variations can define the amount, degree, or quality of protection (and degree of plasticity) offered by the cutin layer to the plant or plant organ against environmental and/or biotic stressors. Cutin is formed from a mixture of polymerized mono- and/or polyhydroxy fatty acids and embedded cuticular waxes. Among the hydroxy fatty acids, polyhydroxy fatty acids (e.g., dihydroxy fatty acids or trihydroxy fatty acids), once esterified, can in some cases form tightly bound networks with high crosslink density and lower permeability as compared to monohydroxy fatty acids and can thereby provide better protection against environmental stressors.

Embodiments described herein relate generally to plant extract compositions and to methods of preparing plant extract compositions that include fatty acid esters (monomers and/or their oligomers) derived from cutin or other crosslinked polyesters. In particular, methods described herein allow for generation of fatty acid esters directly by treating a crosslinked polyester (e.g., cutin) which includes a mixture of polymerized mono- and/or polyhydroxy fatty acids with an acid and an alcohol. Compositions which include the resulting fatty esters can, for example, be subsequently applied to other plant or agricultural products in order to form a protective material (e.g., a coating) over the products, or to enhance or modify existing coatings (either naturally occurring or deposited coatings) which are on the outer surface of the products. The applied coatings can, for example, serve to protect the products from biotic stressors such as bacteria, fungi, viruses, and/or pests. The applied coatings can also (or alternatively) serve to increase the shelf life of produce without refrigeration, and/or to control the rate of ripening or respiration of produce.

Conventional methods for producing fatty acid esters typically involve performing a first step (or series of steps) to isolate fatty acids (e.g., fatty acid monomers and/or oligomers) and then subsequently perform a second step (or series of steps) to convert the fatty acids to esters, for example via Fischer esterification. Methods described herein provide for a process for generating fatty acid esters directly from a polyester such as cutin, without the need to first isolate the fatty acid monomers/oligomers. Accordingly, methods of preparing a composition comprising fatty acid esters can include (i) providing a crosslinked polyester (e.g., cutin) comprising fatty acids, (ii) treating the polyester with an acid and an alcohol, and (iii) removing the acid and alcohol to isolate the resulting fatty acid esters. In particular embodiments described herein, the crosslinked polyester is cutin derived from plant matter.

As used herein, "plant matter" refers to any portion of a plant, including, for example, fruits (in the botanical sense, including fruit peels and juice sacs), leaves, stems, barks, seeds, flowers, peels, or roots.

A first method 100 for treating (e.g., depolymerizing) cutin to obtain a plant extract composition is illustrated in FIG. 1. The method 100 includes first treating plant matter to at least partially separate a cutin-containing portion from a non-cutin-containing portion of the plant matter (step 102). Treating the plant matter can include, for example, thermal treating of the plant matter. The thermal treating can include, for example, heating the plant matter (e.g., with steam, in water or in another solvent), freezing the plant, subjecting the plant matter to cyclic thermal treatments, or drying. The plant matter can include any suitable plant matter or other agricultural product such as, for example, fruits (including fruit peels and juice sacs), leaves, stems, barks, seeds, flowers, peels, or roots. In some embodiments, the plant matter can include agricultural waste products such as, for example, tomato peels, grape skins, apple peels, pepper peels, lemon peels, lemon leaf, lime peels, lime leaf, orange peels, orange leaf, orange fruit, clementine leaf, clementine fruit, mandarin leaf, mandarin fruit, pea seeds, grapefruit peels, grapefruit leaf, grapefruit seeds, papaya peels, cherry fruits, cranberry skins, coffee cherries, grass clippings, or any other plants or portions of plants that can yield any embodiment of the plant extract compositions described herein. In some embodiments, the plant matter can be a fruit (e.g., a tomato, cranberry, or grape) and the cutin-containing portion can be a peel of the fruit (e.g., a tomato peel or cranberry skin or grape skin) such that the boiling can at least partially separate the peel from the fruit. The fruit can be washed to remove surface residue, waxes, or other debris before operation 102. Furthermore, the fruit can be cut into halves, quarters, or small pieces or ground to finer pieces and then boiled until the peels or skins are visibly separated from the fruit pulp.

The method 100 can optionally include mechanically processing the plant matter to at least partially separate the cutin-containing portion from the non-cutin-containing portion of the plant matter (step 104). The mechanical process can be performed before and/or after thermal treatment of the plant matter (i.e., 102) (e.g., boiling of the plant matter in water) to facilitate separation of the cutin-containing portion from the non-cutin-containing portion of the plant matter. Suitable mechanical processes can include, for example, centrifugation, (ultra)sonication, pressing, ball milling, grinding, etc. In some embodiments, mechanical separation can include separating a fruit peel from the fruit pulp. In some embodiments, mechanical removal of the pulp might not be performed and the fruit skins (e.g., waste fruit skins left over after processing of the fruit) may be macerated, blended, cut, shredded, food processed, or otherwise subjected to some other mechanical treatment operation to physically break down the fruit skins into smaller or finer pieces. In some embodiments, a plurality of intermediate mechanical processes can be used to obtain the plant extract composition. For example, a mechanical step can be used to separate the cutin from the non-cutin-containing portion, as described herein, or be used to augment any other operation included in the method 100. Such mechanical processes can include any of the mechanical processes described herein such as, for example, centrifugation, sonication, (ultra)sonication, milling, grinding, filtration, etc.

The cutin-containing portion is then optionally heated (e.g., boiled) in a mixture of ammonium oxalate and oxalic acid to separate the cutin from the non-cutin-containing portion (step 106). Optionally this process can also be achieved (or assisted) using enzymes capable of breaking down polysaccharides or pectin. For example, the cutin can include the cuticular layer of the plant matter. The heating in the ammonium oxalate and oxalic acid mixture disrupts the pectinaceous glue that attaches the cuticle to the underlying cells of the plant matter and helps release the cuticle. Furthermore, this step disrupts the pectinaceous glue that is found within primary cell walls and between plant cells (e.g., in the middle lamella that binds neighboring cells), aiding in the isolation of a cutin-containing portion. In this manner, the ammonium oxalate and oxalic acid solution can facilitate at least partial chemical detachment of remaining debris from the cutin-containing portion of the plant (e.g., removal of any remaining pulp from the fruit peel). The heating can be performed at any suitable temperature (e.g., 35 degrees Celsius, 50 degrees Celsius, 55 degrees Celsius, 60 degrees Celsius, 65 degrees Celsius, 70 degrees Celsius, 75 degrees Celsius, 80 degrees Celsius, 85 degrees Celsius, 90 degrees Celsius, 95 degrees Celsius, or 100 degrees Celsius, inclusive of all ranges and values therebetween) and for any suitable time (this process can be accelerated if carried out under elevated pressure). For example, in some embodiments, the cutin-containing portion can be heated in the mixture of ammonium oxalate and oxalic acid at a temperature of about 75 degrees Celsius for about 24 hours. In some embodiments, the portion of the plant, for example, the fruit peel, after treatment with the ammonium oxalate and oxalic acid solution, can be isolated by filtration and dried (e.g., air-dried under ambient conditions, oven-dried or freeze-dried) to remove any residual water.

In some embodiments, the cutin can optionally be treated with an enzyme (step 108). For example, the cutin can be treated with an enzyme such as a carbohydrate-hydrolyzing enzyme to digest or otherwise remove carbohydrates (e.g., cellulose or pectin) attached to or embedded within the cutin. Such enzymes can include, for example, naturally derived or synthetic cellulases, pectinases, and hemicellulases. The enzymatic degradation can be used before, after, or otherwise in place of step 106 to obtain the cutin from the non-cutin-containing portion. In some embodiments, the reverse process may be employed, wherein the cutin is treated with an enzyme that can at least partially depolymerize the cutin to yield any combination of cutin-derived oligomers and cutin-derived monomers and to leave behind the non-cutin-containing components, which could be filtered out or otherwise separated. Such enzymes can include, for example, cutinases, esterases, or lipases.

Optionally, the cutin is refluxed or subjected to soxhlet extraction in at least one suitable solvent (e.g., chloroform and/or methanol) to remove soluble waxes or polar impurities from the cutin (step 110). For example, the cutin can be refluxed or subjected to soxhlet extraction only in chloroform, refluxed or soxhlet extracted in chloroform followed by refluxing or soxhlet extraction in methanol, refluxed or subjected to soxhlet extraction only in methanol, or refluxed or subjected to soxhlet extraction in a mixture of chloroform and methanol, or any other suitable solvent(s) (or combinations thereof) in which the wax and/or polar components are soluble. In some embodiments, the cutin can be refluxed in a dilute solution of a strong base (e.g., potassium hydroxide in water or in alcoholic solvent), or a solution of a moderately strong or weak base (e.g., potassium carbonate in water or in alcoholic solvent) to remove soluble pigmented impurities. Alternatively, removal of residual waxes and remaining soluble components can be achieved using supercritical $CO_2$ or supercritical $H_2O$. The refluxing can be performed at any suitable temperature and for any suitable length of time. For example, in some embodiments, the cutin can be refluxed in chloroform at about 60-65 degrees Celsius for about 24-36 hours to remove any wax and/or non-polar compounds embedded in the cutin. This can be followed by refluxing in methanol at 65-70 degrees Celsius for about 4-12 hours, for example, to remove any polar organic components (e.g., flavonoids and flavonoid glycosides) present in the cutin. The completion of the operation can be determined by the clarity of solvents. For example, the process can be monitored with instrumentation (e.g., NMR, GC-MS, React-IR, FTIR, spectrophotometry, etc.) configured to analyze the clarity of the solvents and can continue until a predetermined clarity is achieved. Each of the chloroform and/or methanol extraction processes can be performed in any apparatus capable of refluxing (i.e., recirculating and/or recycling) the solvents such as, for example, a reaction flask equipped with a condenser, a Soxhlet apparatus, a Kumagawa extractor, an ultrasound assisted extractor, a robot automated extractor, or any other suitable extraction apparatus. Such an apparatus can, for example, reduce the amount of solvent used in the extraction process. Any other solvent or combinations thereof (i.e., a binary or ternary mixture) can be used to wash out undesired impurities. Suitable solvents can include, for example, diethyl ether, dichloromethane, hexane, petroleum ether, ethyl acetate, acetone, isopropanol, ethanol, acetonitrile, supercritical carbon dioxide, supercritical water, water, and mixtures thereof. In some embodiments, multiple extraction steps in one or more solvents can also be performed. In some embodiments, intermediate enzymatic treatment steps can also be performed between the solvent extraction processes, for example, to liberate undesired compounds from the cutin. The solution obtained after operation 110 can include a relatively pure sample of the cutin included in the portion of the plant along with any residually attached or embedded polysaccharides (e.g., cellulose), plant metabolites (e.g., flavonoids), and/or proteins.

The cutin is then heated in a base solution (e.g., metal alkoxide or metal hydroxide dissolved in a solvent such as ethanol or methanol or water or combinations thereof) to at least partially depolymerize the cutin and obtain a plant extract including a plurality of cutin-derived monomers, oligomers, or combinations thereof (step 112). The pH of the solution can, for example, be in a range of about 10 to 14, for example in a range of 12 to 14. The metal alkoxide can include, for example, sodium methoxide, sodium ethoxide, sodium iso-propoxide, sodium n-propoxide, sodium iso-butoxide, sodium n-butoxide, potassium methoxide, potassium ethoxide, potassium iso-propoxide, potassium n-propoxide, potassium iso-butoxide, or potassium n-butoxide. The metal hydroxide can include, for example, Group I or Group II metal hydroxides, such as lithium, sodium, potassium, calcium, rubidium, or cesium hydroxide. Also included are precursors or compounds that will generate alkoxide or hydroxide in a suitable reaction medium (such as neat metals (e.g., sodium metal) or oxides in methanol, or ammonia in water). Refluxing of the cutin in the presence of the metal alkoxide or metal hydroxide can be performed at any suitable temperature and for any suitable length of time such as, for example, at about 65 degrees Celsius for about 24 hours. In some embodiments, the temperature and/or the refluxing time can be such that the cutin is only partially depolymerized to yield a predetermined combination of oligomers and monomers. In some embodiments, the temperature and/or the refluxing time can be adjusted such that the cutin is mostly depolymerized by the metal alkoxide or metal hydroxide into a plurality of cutin-derived monomers and/or oligomers. In some embodiments, the refluxing in the metal alkoxide or metal hydroxide can be performed in a mixture of the metal alkoxide or metal hydroxide and a solvent, for example, methanol, ethanol, hexane, toluene, etc. In some embodiments, the solvent can include methanol. The concentration of metal alkoxide, solvent, and/or the pH of the solution can, for example, facilitate the preservation of the depolymerized cutin components in monomeric form, which can prevent oligomerization or repolymerization of the liberated cutin monomers included in the plant extract. Although an acid catalyst for the reaction (utilizing methods further described below) could be used in place of the base catalyst, base catalysts are commonly used for transesterification of oils, as in many cases the reaction rate can be higher than that for an acid catalyst.

Figure 2A:
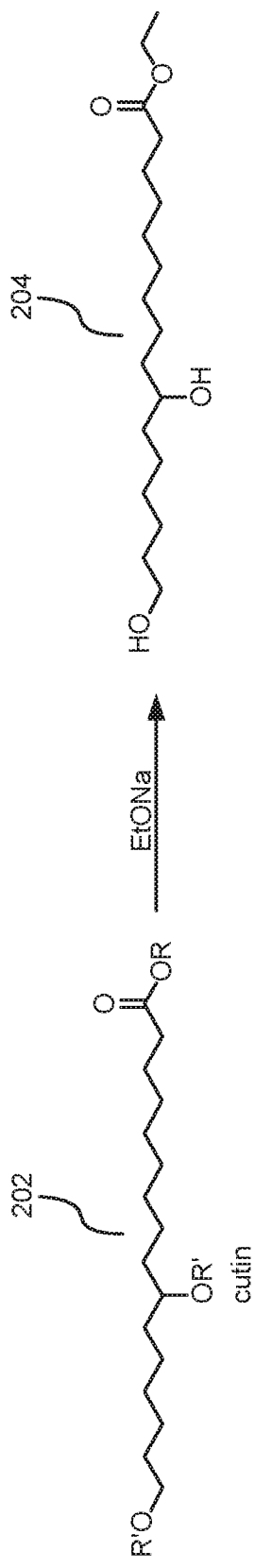
FIGS. 2A and 2B are schematic representations of reactions associated with a step of the method of FIG. 1.

In efforts to obtain fatty acid ester products (or oligomers thereof) from the depolymerization step 112 of method 100, the refluxing of the cutin in the presence of the metal alkoxide was carried out by the inventors of the present disclosure in anhydrous reagents and anhydrous solvents (e.g., ethanol) in a closed, nitrogenous atmosphere. Specifically, cutin obtained from tomato pomace was refluxed in a solution comprising sodium ethoxide (prepared by dissolving sodium in ethanol) according to the process described in Example 2 below in order to favor ester formation over saponification and acid formation. The expected reaction is schematically represented in FIG. 2A for the case of an anhydrous solution comprising sodium ethoxide dissolved in ethanol. Referring to FIG. 2A, cutin 202 is represented by a crosslinked network of polyhydroxy fatty acids, where R and R' represent adjacent fatty acid units. Depolymerization of the cutin 202 by the sodium ethoxide present in the EtOH in the absence of water is expected to form isolated ethyl esters 204, as shown in FIG. 2A.

Figure 2B:
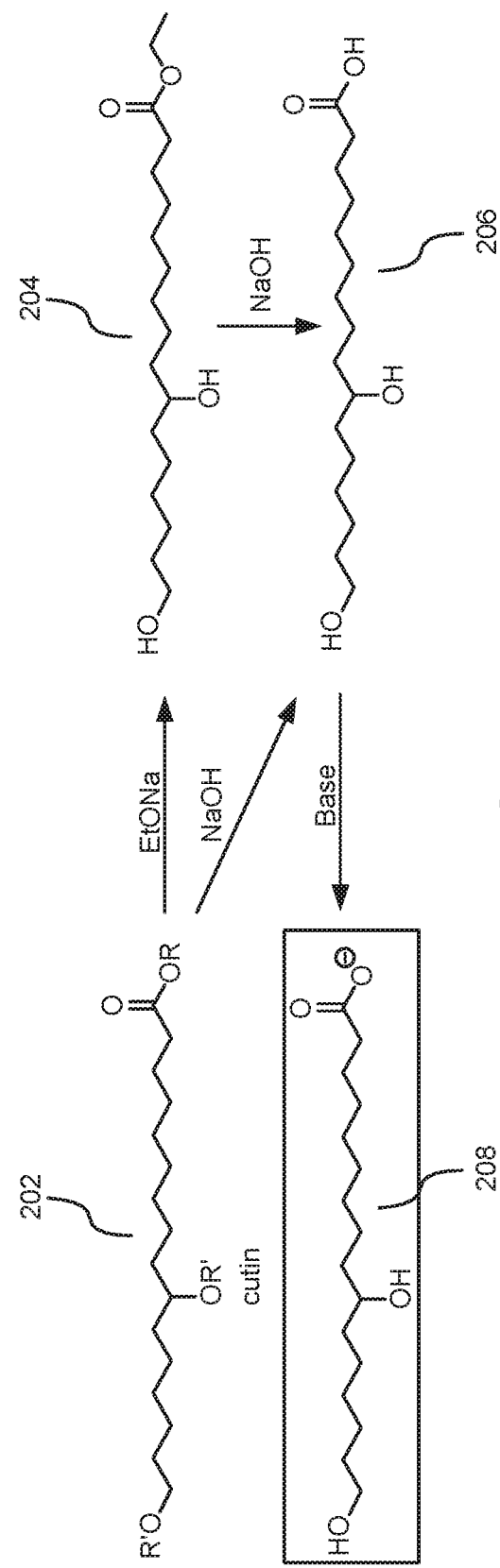

FIG. 2B is a schematic representation of the depolymerization reaction for the case where water is present in the solution. In this case, the reaction produces both ethyl esters 204 and carboxylic acid 206. As further shown in FIG. 2B, the base in the solution causes the carboxylic acid 206 to be converted to carboxylate 208. If enough water is present in the solution, substantially all of the depolymerized product is driven to the carboxylic acid 206 and then converted to the carboxylate 208 by the base in the solution, such that no measurable concentration of ethyl esters 204 is present in the resulting composition.

Without wishing to be bound by theory, the inventors of the current disclosure observed that despite extensive drying and/or other efforts to ensure that no water was present in the reaction during cutin depolymerization according to Example 2, the apparently dry cutin appeared to contain sufficient endogenous water to result in all of the depolymerized product being shunted to the carboxylate 208. Consequently, no substantial concentration of esters 204 could be detected in the resulting extract composition.

Figure 3:
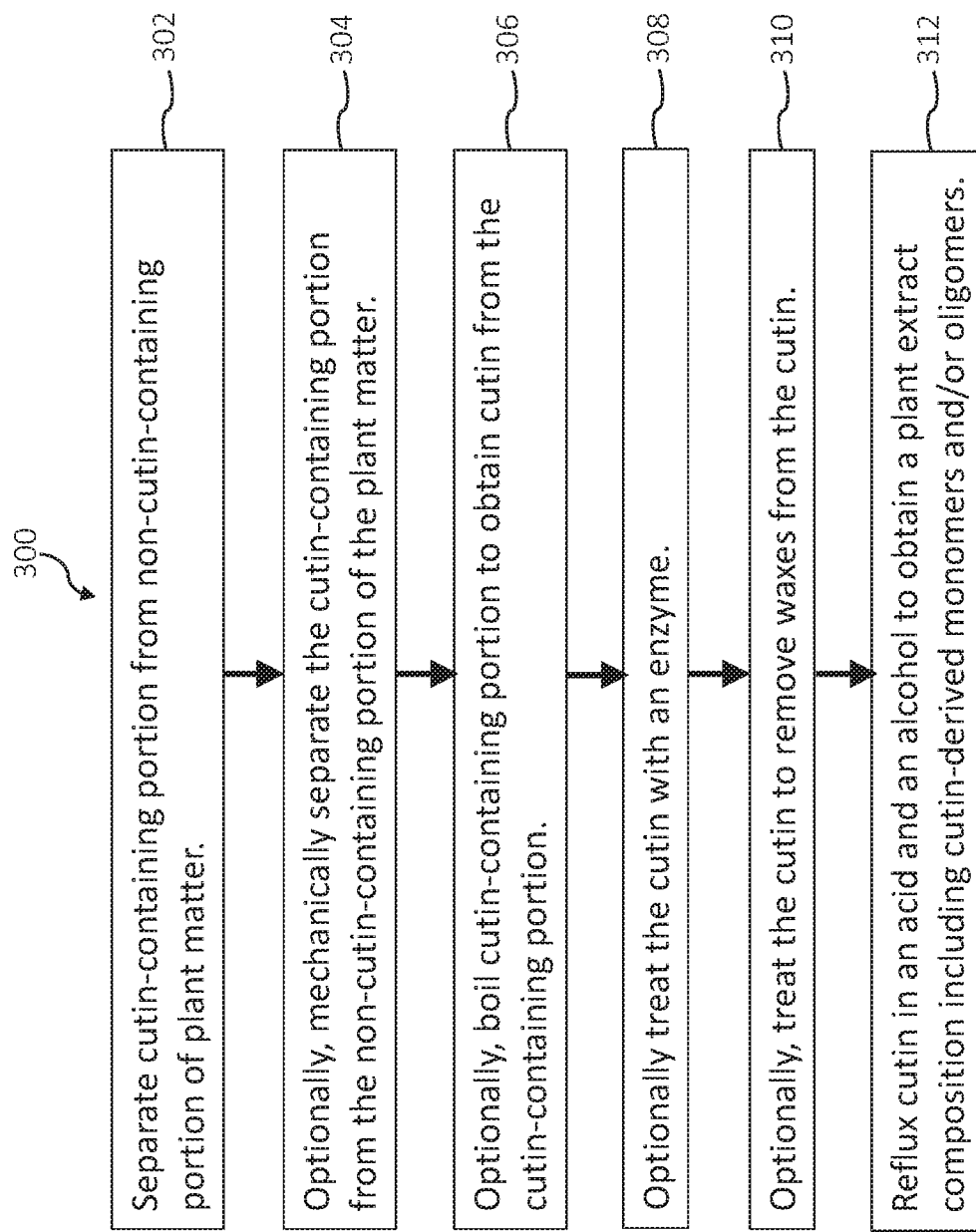
FIG. 3 is a schematic flow diagram of a second exemplary method for preparing a composition.

A second method 300 for depolymerizing cutin to obtain a plant extract composition is illustrated in FIG. 3. Steps 302, 304, 306, 308, and 310, in which cutin is obtained from plant matter, are the same as steps 102, 104, 106, 108, and 110, respectively, of method 100 in FIG. 1. However, in step 312 of method 300, the cutin is refluxed in an acid and an alcohol (rather than a base and an alcohol as in step 112 of method 100) in order to obtain a plant extract composition including cutin-derived monomers and/or oligomers.

Figure 4:
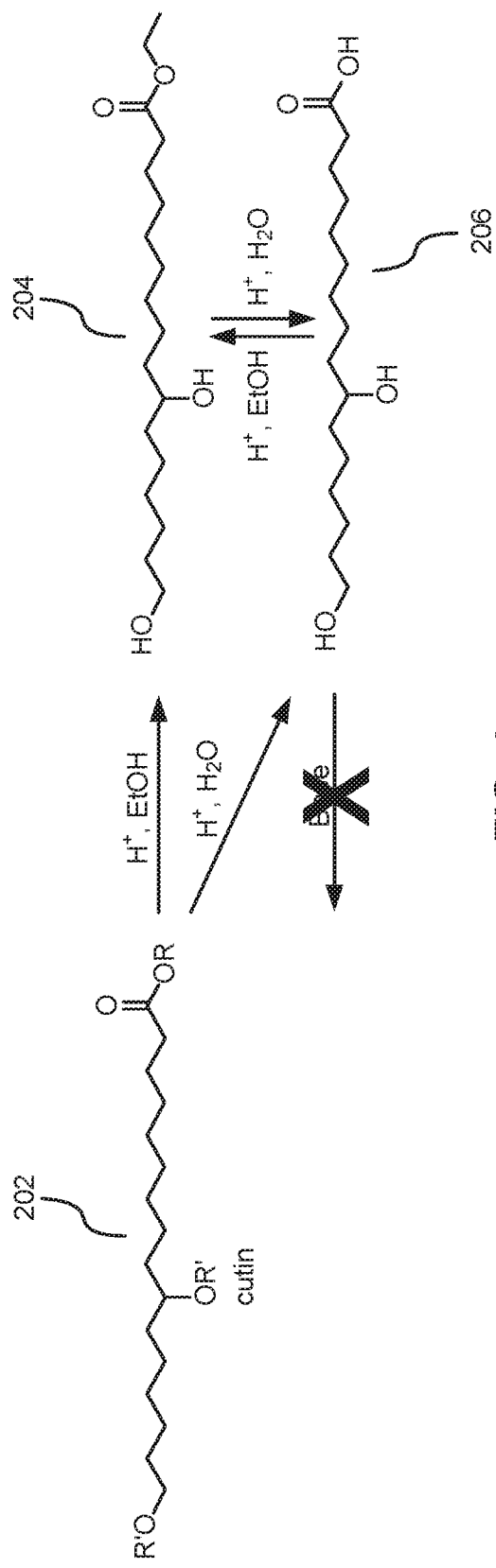
FIG. 4 is a schematic representation of a reaction associated with a step of the method of FIG. 3.

The specific reaction associated with the second method 300, and specifically with step 312, is schematically represented in FIG. 4 for the case of a solution comprising an acid dissolved in ethanol. The reaction in FIG. 4 assumes the presence of water in the solution (e.g., endogenous water contained within the cutin). Similar to FIG. 2, in FIG. 4 cutin 202 is represented by a crosslinked network of polyhydroxy fatty acids, where R and R' represent adjacent fatty acid units. Depolymerization of the cutin 202 in the acidified solution in the presence of water is expected to form ethyl esters 204 and carboxylic acid 206 in a state of equilibrium with one another, thus producing a plant extract composition including fatty acid esters (e.g., ethyl esters 204). In step 312 of method 300, due to the absence of a base catalyst, the carboxylic acid 206 is not converted to a carboxylate, as in method 100 and corresponding FIG. 2B. Consequently, the reaction is expected to produce a composition comprising a mix of ethyl esters 204 and carboxylic acid 206, where the product distribution approximately reflects the ratio of esterification partner to water.

Figure 6:
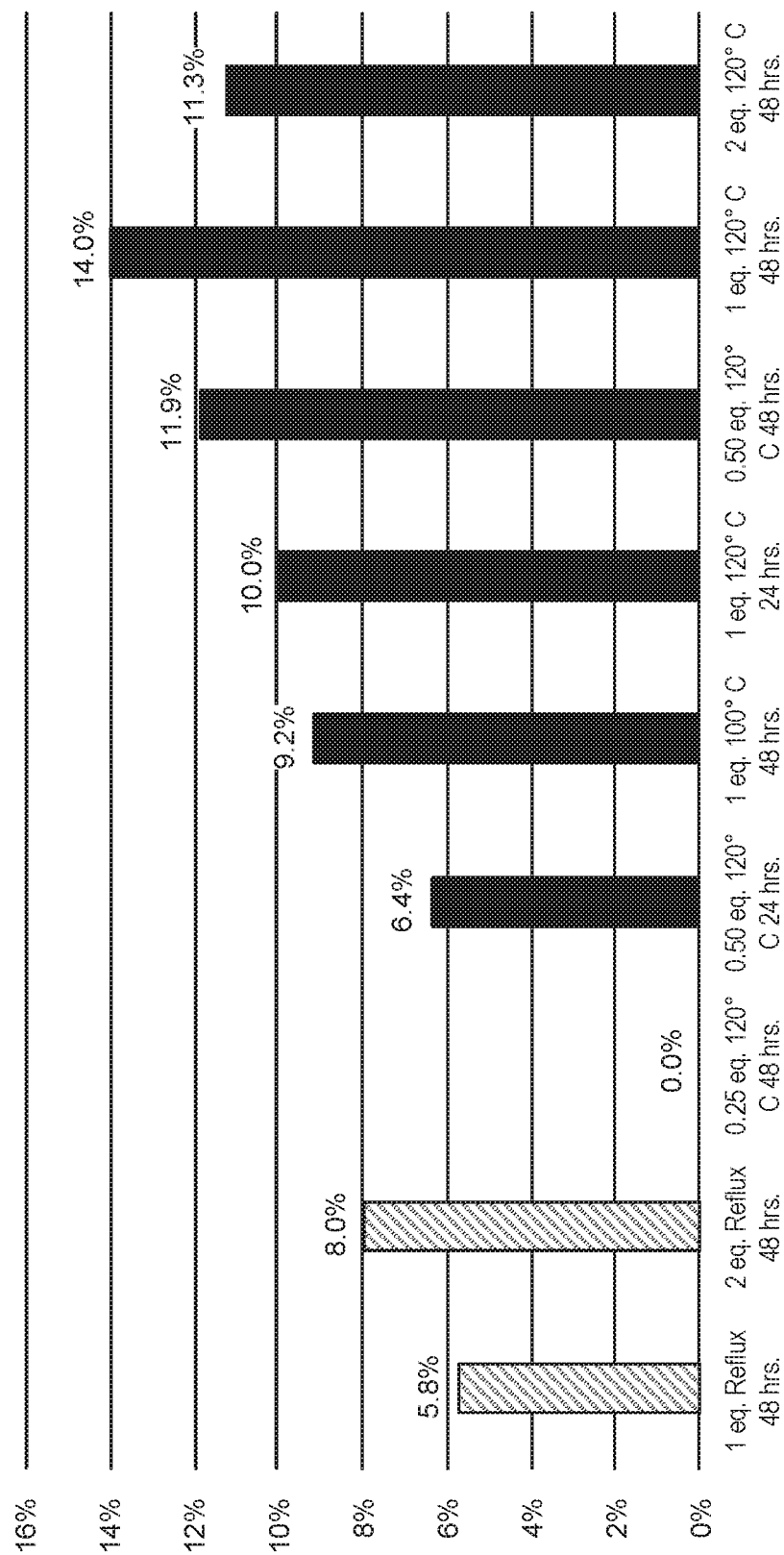

In efforts to obtain a composition including fatty acid esters (or oligomers thereof) by way of method 300 (and in particular by utilizing step 312 of method 300), the inventors of the subject matter in the current application refluxed cutin obtained from tomato pomace in a solution comprising sulfuric acid dissolved in ethanol according to the process described in Example 3 below. Results are illustrated in FIGS. 5 and 6. As shown in Example 3 and FIGS. 5 and 6, the process resulted in the production and isolation of ethyl 10,16-dihydroxyhexdecanoate (herein "EtDHPA").

It was found through extensive experimentation that a larger amount of acid than predicted from catalytic calculations was needed to ensure high yields of products. For instance, under refluxing conditions, an increase in both crude isolate and purified isolate was seen when increasing the equivalence of sulfuric acid used from 0.1 to 0.25 to 0.5 to 1 to 2 equivalents, from negligible material to 8.1% isolated yield, over the course of 48 hours. Furthermore, the reaction could additionally be accelerated by sealing the system to generate pressure, such that the reaction could be conducted above the atmospheric boiling point of the solvent (see Example 4). A further increase in crude isolate and purified isolate yields was seen when the temperature was increased from reflux (78° C.) to 100° C. to 120° C., with one equivalent of acid, up to 14% isolated yield. However, without wishing to be bound by theory, there appears to be an upper limit, after which the isolated yield appears to decrease, as seen in FIGS. 5 and 6 (120° C., 2 eq. $H_2SO_4$, 48 hrs).

Figure 7A:
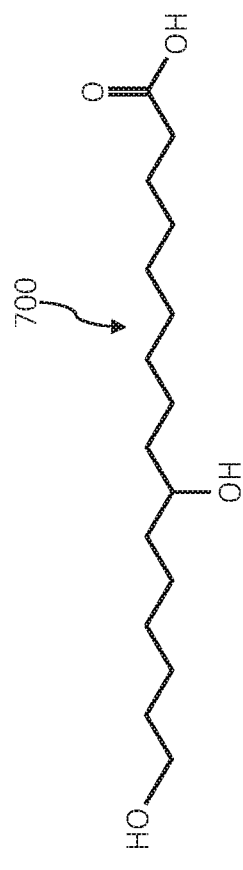
FIGS. 7A, 7B, 7C, 7D, 7E, 7F, 7G, and 7H show the chemical structure of 10,16-dihydroxyhexadecanoic acid, 10,18-dihydroxyoctadecanoic acid, 9,16-dihydroxyhexadecanoic acid, 9,18-dihydroxyoctadecanoic acid, 9,10,16-trihydroxyhexadecanoic acid, 9,10,18-trihydroxyoctadecanoic acid, 9,10-epoxy-16-hydroxyhexadecanoic acid, and 9,10-epoxy-18-hydroxyoctadecanoic acid, respectively.
Figure 7C:
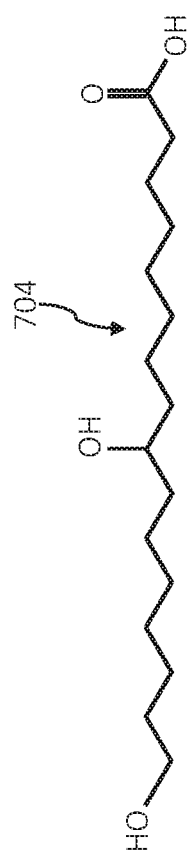
Figure 7E:
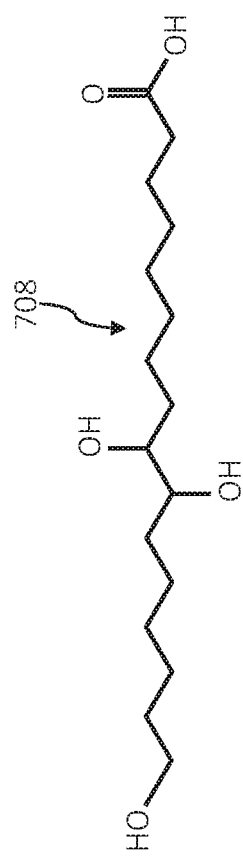
Figure 7G:
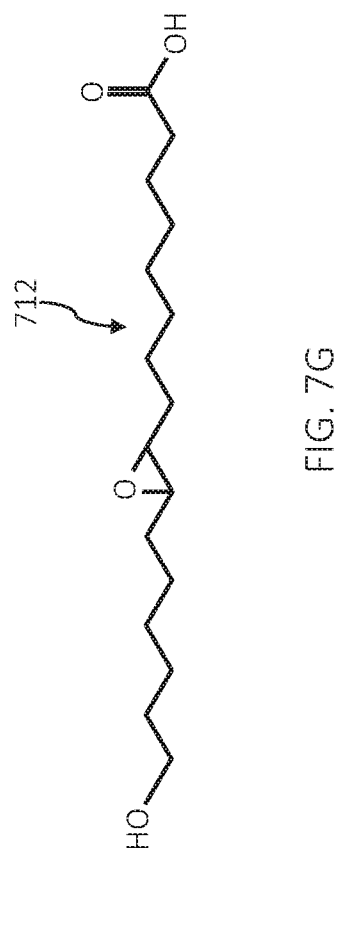
Figure 8A:
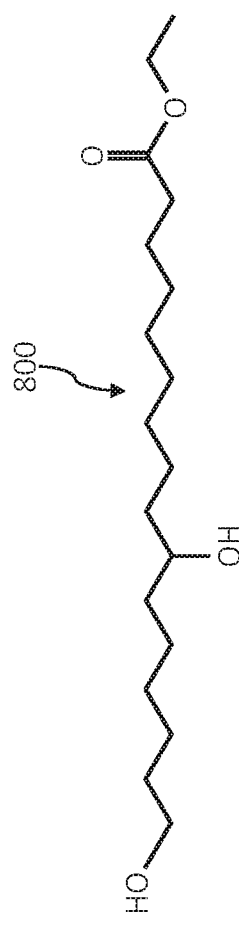
Figure 8B:
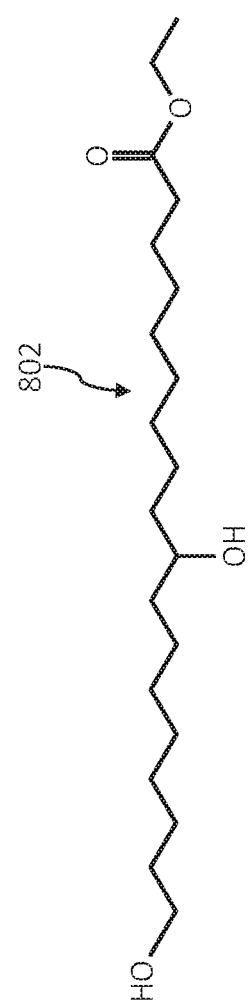
Figure 8E:
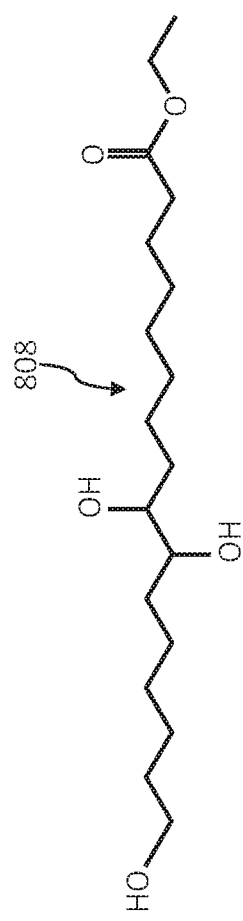
Figure 8F:
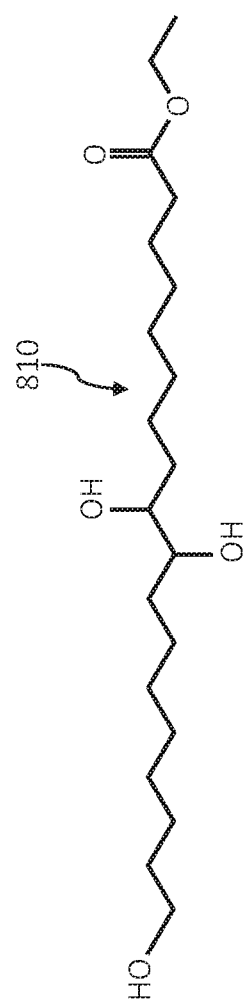
Figure 8G:
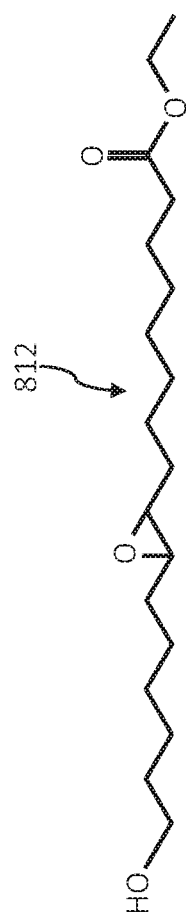

While EtDHPA 204 (in FIG. 4) can be produced by method 300 of FIG. 3 with ethanol utilized as the alcohol and with a cutin source (or other crosslinked polymer) that includes 10,16-dihydroxyhexadecanoic acid (or esters thereof) as a building block of the crosslinked network, other types of ethyl esters can be produced by method 300 using cutin from plant sources (or other crosslinked polymers/networks) that are formed of different molecular building blocks. For example, cutin from tomatoes tends to have a high proportion of $C_{16}$ fatty acids (e.g., fatty acids having a carbon chain length of 16) such as that of FIGS. 7A, 7C, 7E, and 7G, where FIG. 7A shows the chemical composition of 10,16-dihydroxyhexadecanoic acid (700 in FIG. 7A), FIG. 7C shows the chemical composition of 9,16-dihydroxyhexadecanoic acid (704 in FIG. 7C), FIG. 7E shows the chemical composition of 9,10,16-trihydroxyhexadecanoic acid (708 in FIG. 7E), and FIG. 7G shows the chemical composition of 9,10-epoxy-16-hydroxyhexadecanoic acid (712 in FIG. 7G). Accordingly, ethyl esters that can be produced by method 300 using cutin from tomatoes can include ethyl 10,16-dihydroxyhexadecanoate (800 in FIG. 8A), ethyl 9,16-dihydroxyhexadecanoate (804 in FIG. 8C), ethyl 9,10, 16-trihydroxyhexadecanoate (808 in FIG. 8E), and/or ethyl 9,10-epoxy-16-hydroxyhexadecanoate (812 in FIG. 8G).

Figure 7B:
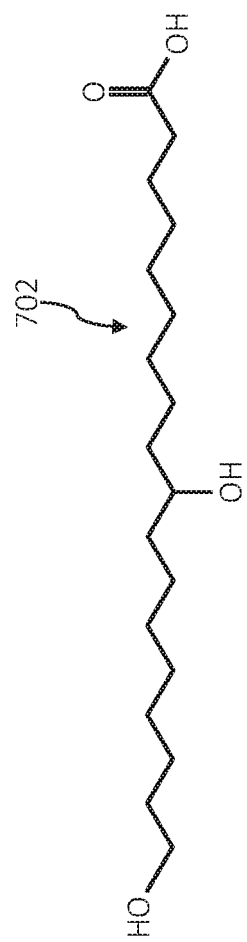
Figure 7D:
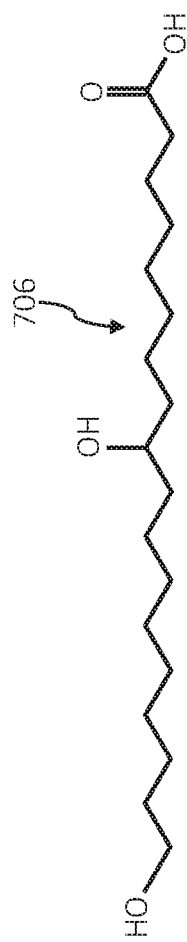
Figure 7F:
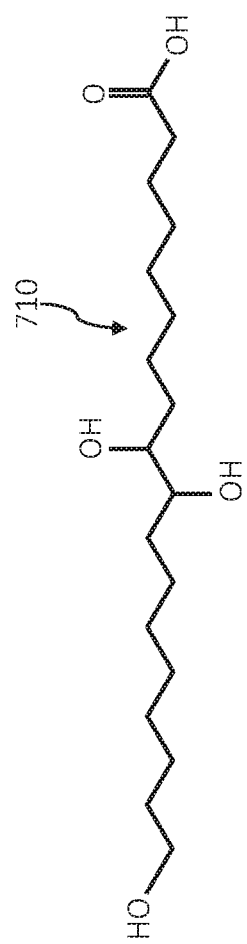
Figure 7H:
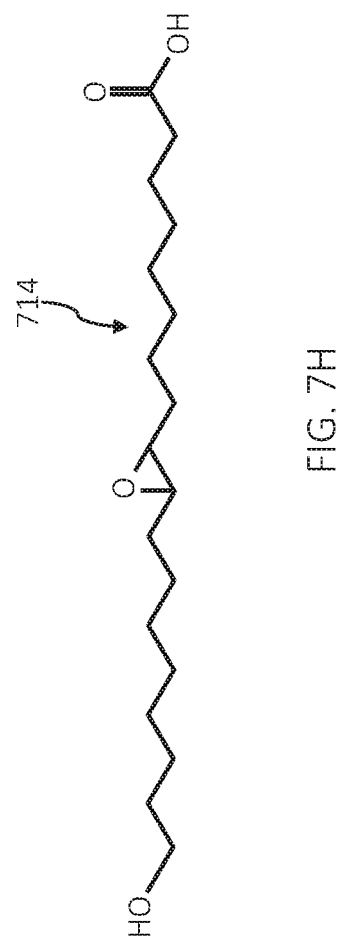
Figure 8H:
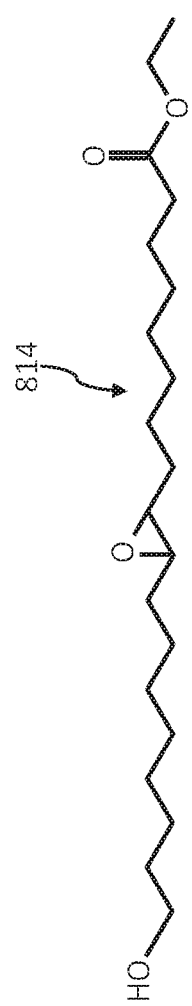

On the other hand, cutin from cranberries tends to have a high proportion of Cis fatty acids (e.g., fatty acids having a carbon chain length of 18) such as that of FIGS. 7B, 7D, 7F, and 7H, where FIG. 7B shows the chemical composition of 10,18-dihydroxyoctadecanoic acid (702 in FIG. 7B), FIG. 7D shows the chemical composition of 9,18-dihydroxyoctadecanoic acid (706 in FIG. 7D), FIG. 7F shows the chemical composition of 9,10,18-trihydroxyoctadecanoic acid (710 in FIG. 7F), and FIG. 7H shows the chemical composition of 9,10-epoxy-18-hydroxyoctadecanoic acid (714 in FIG. 7H). Accordingly, ethyl esters that can be produced by method 300 using cutin from cranberries can include ethyl 10,18-dihydroxyoctadecanoate (802 in FIG. 8B), ethyl 9,18-dihydroxyhexadecanoate (806 in FIG. 8D), ethyl 9,10,18-trihydroxyoctadecanoate (810 in FIG. 8F), and/or ethyl 9,10-epoxy-18-hydroxyoctadecanoate (814 in FIG. 8H).

Figure 9A:
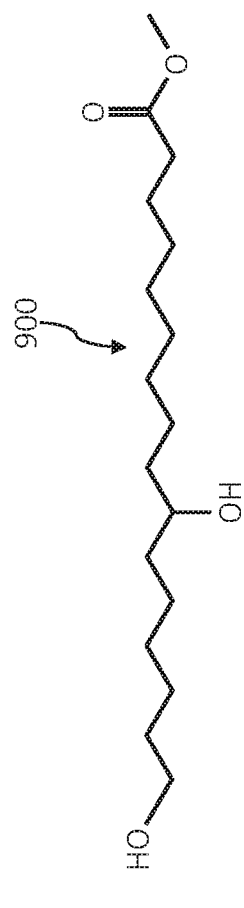
FIGS. 9A, 9B, 9C, 9D, 9E, 9F, 9G, and 9H show the chemical structure of methyl 10,16-dihydroxyhexadecanoate, methyl 10,18-dihydroxyoctadecanoate, methyl 9,16-dihydroxyhexadecanoate, methyl 9,18-dihydroxyoctadecanoate, methyl 9,10,16-trihydroxyhexadecanoate, methyl 9,10,18-trihydroxyoctadecanoate, methyl 9,10-epoxy-16-hydroxyhexadecanoate, and methyl 9,10-epoxy-18-hydroxyoctadecanoate, respectively.
Figure 9B:
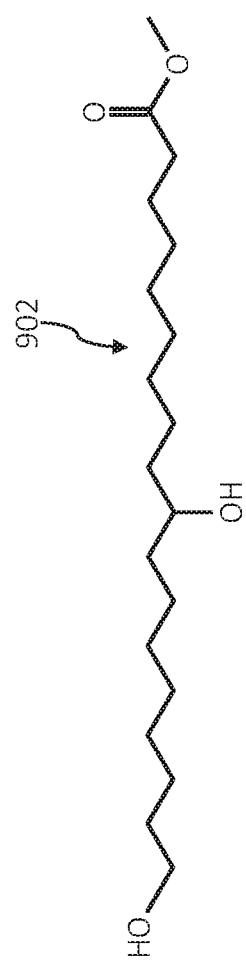
Figure 9C:
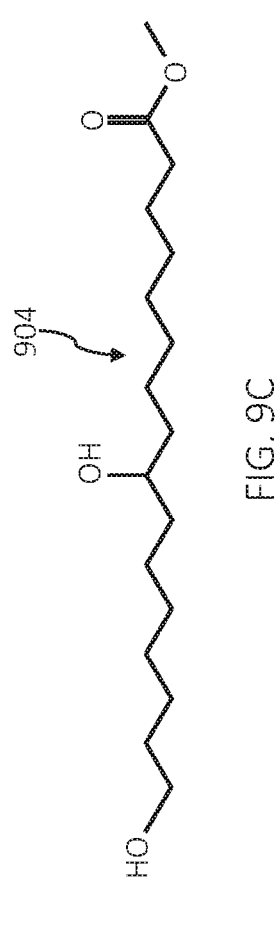
Figure 9D:
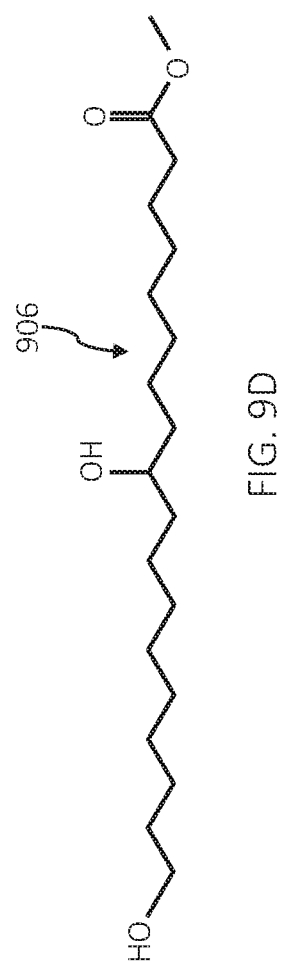
Figure 9E:
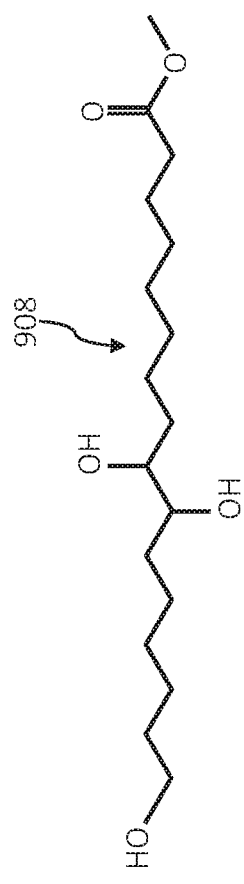
Figure 9F:
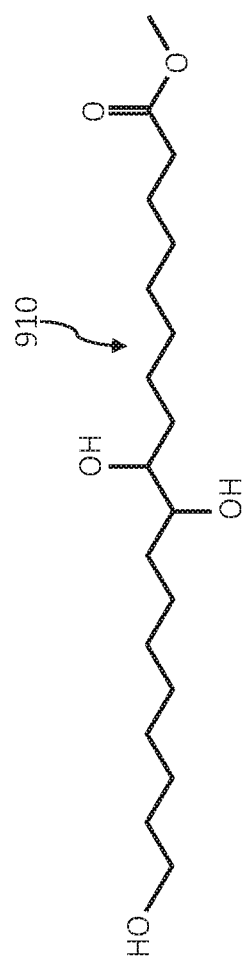
Figure 9G:
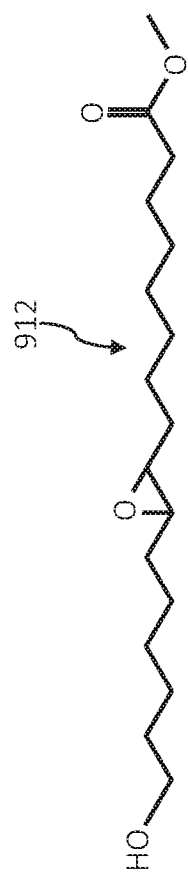
Figure 9H:
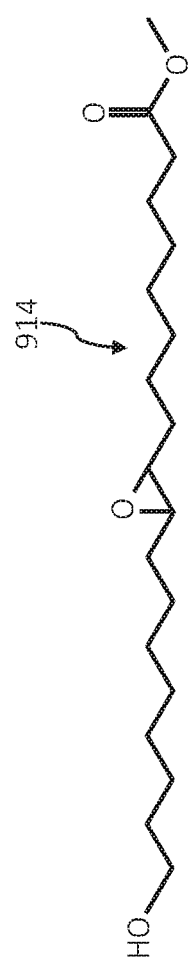
Figure 10A:
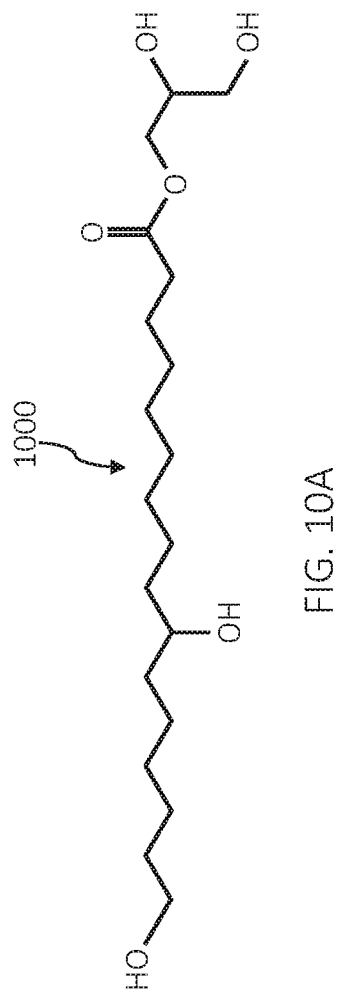
FIGS. 10A, 10B, 10C, 10D, 10E, 10F, 10G, and 10H show the chemical structure of 2,3-dihydroxypropyl 10,16-dihydroxyhexadecanoate, 2,3-dihydroxypropyl 10,18-dihydroxyoctadecanoate, 2,3-dihydroxypropyl 9,16-dihydroxyhexadecanoate, 2,3-dihydroxypropyl 9,18-dihydroxyhexadecanoate, 2,3-dihydroxypropyl 9,10,16-trihydroxyhexadecanoate, 2,3-dihydroxypropyl 9,10,18-trihydroxyoctadecanoate, 2,3-dihydroxypropyl 9,10-epoxy-16-hydroxyhexadecanoate, and 2,3-dihydroxypropyl 9,10-epoxy-18-hydroxyoctadecanoate, respectively.
Figure 10B:
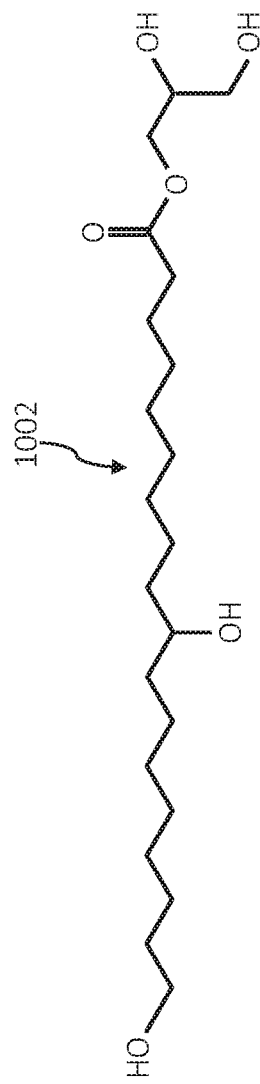
Figure 10C:
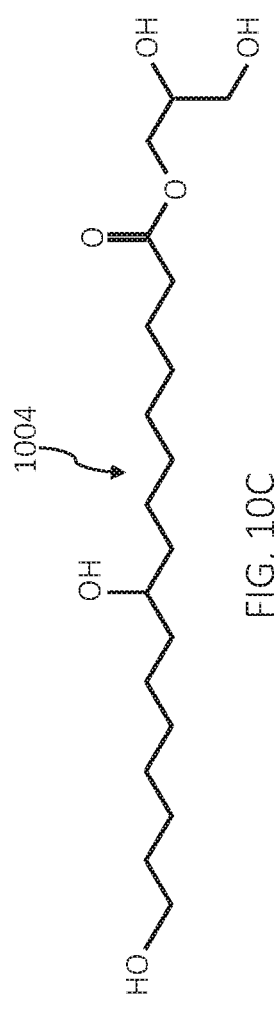
Figure 10D:
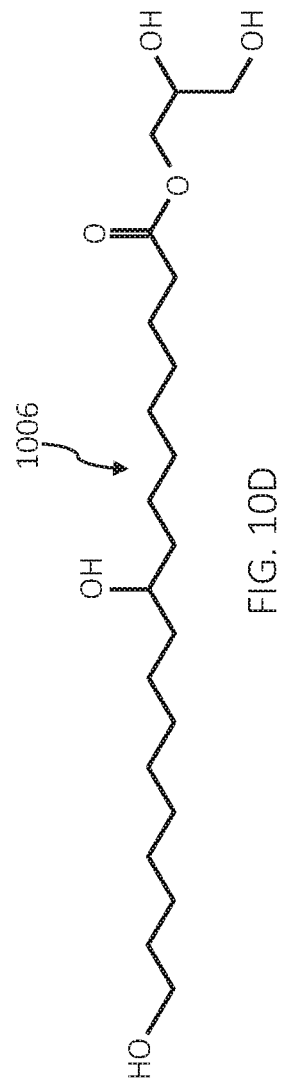
Figure 10E:
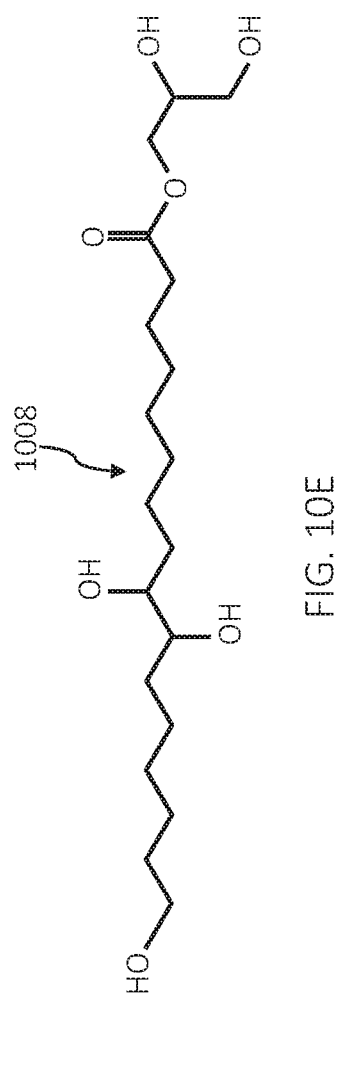
Figure 10F:
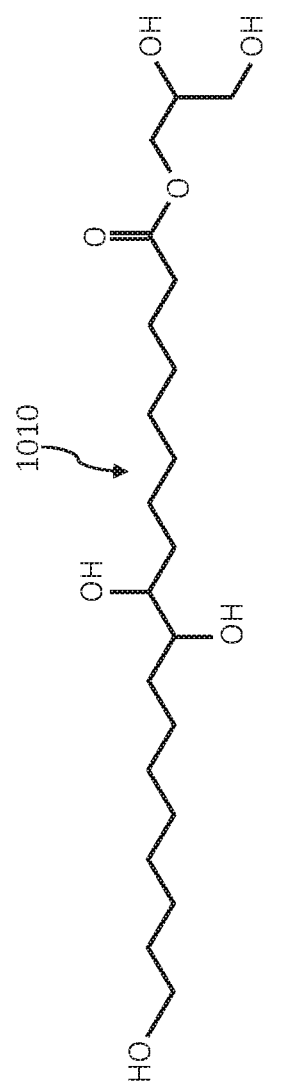
Figure 10G:
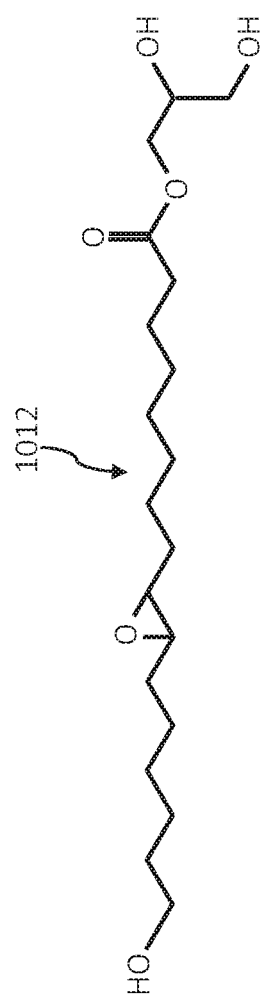
Figure 10H:
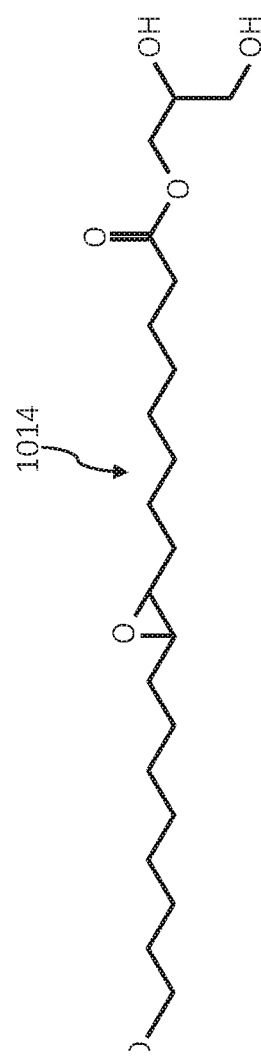
Figure 11A:
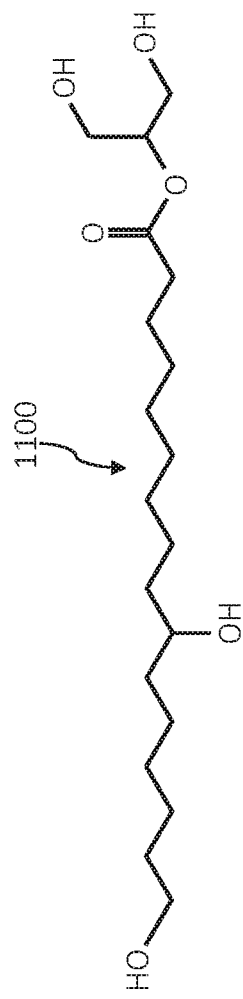
FIGS. 11A, 11B, 11C, 11D, 11E, 11F, 11G, and 11H show the chemical structure of 1,3-dihydroxypropan-2-yl 10,16-dihydroxyhexadecanoate, 1,3-dihydroxypropan-2-yl 10,18-dihydroxyoctadecanoate, 1,3-dihydroxypropan-2-yl 9,16-dihydroxyhexadecanoate, 1,3-dihydroxypropan-2-yl 9,18-dihydroxyhexadecanoate, 1,3-dihydroxypropan-2-yl 9,10,16-trihydroxyhexadecanoate, 1,3-dihydroxypropan-2-yl 9,10,18-trihydroxyoctadecanoate, 1,3-dihydroxypropan-2-yl 9,10-epoxy-16-hydroxyhexadecanoate, and 1,3-dihydroxypropan-2-yl 9,10-epoxy-18-hydroxyoctadecanoate, respectively.
Figure 11B:
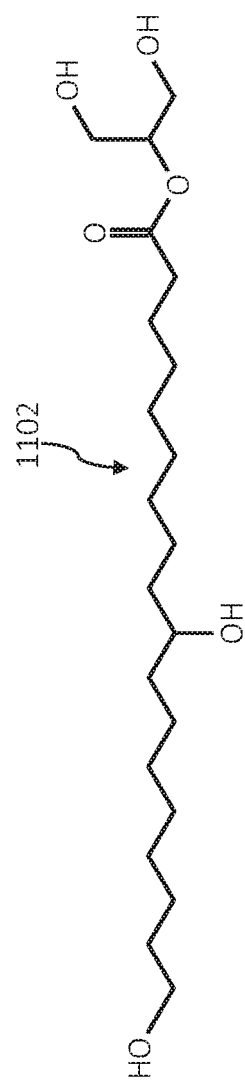
Figure 11C:
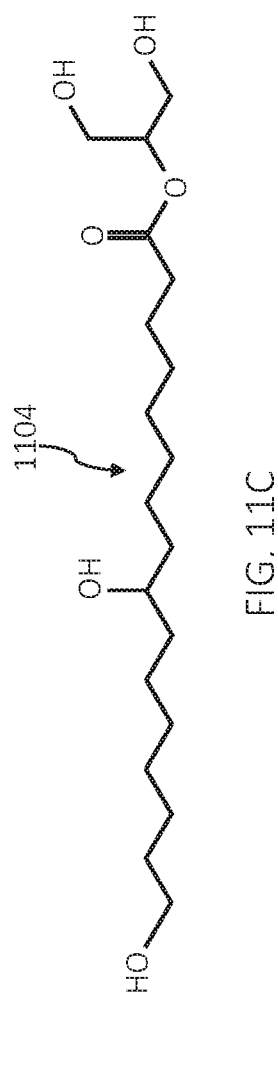
Figure 11D:
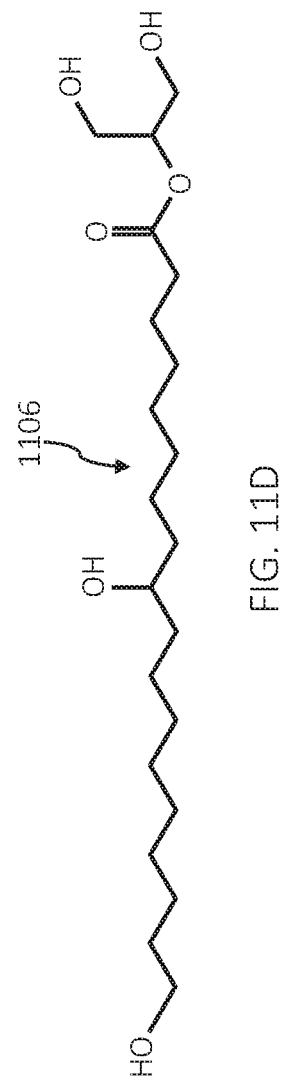
Figure 11E:
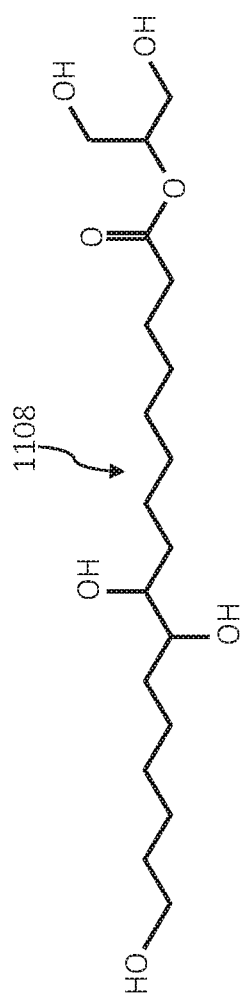
Figure 11F:
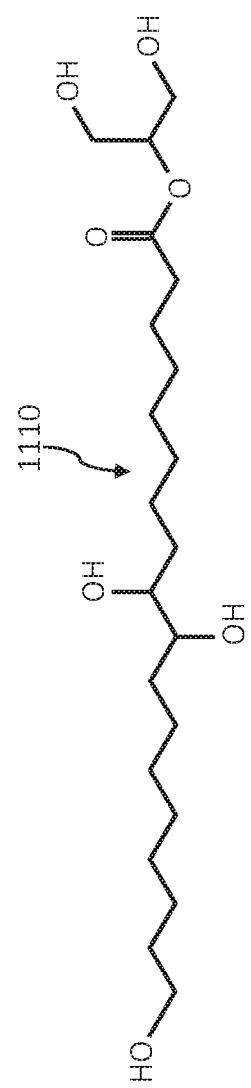
Figure 11G:
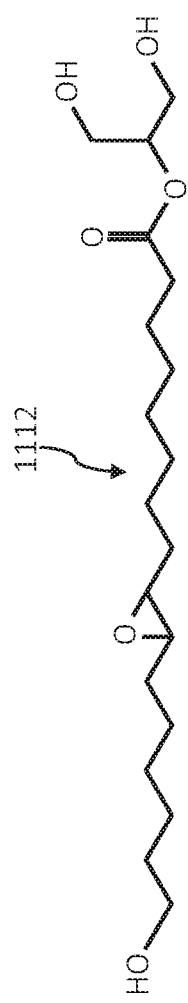
Figure 11H:
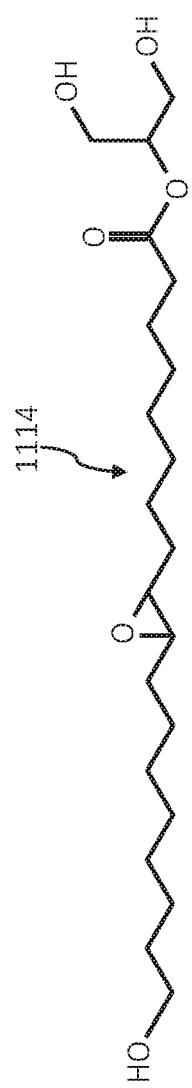

Furthermore, alcohols other than (or in addition to) ethanol can be used in the method 300 of FIG. 3, which can result in other types of esters being produced. For example, using methanol as the alcohol can result in the production of methyl esters such as methyl 10,16-dihydroxyhexadecanoate (900 in FIG. 9A), methyl 10,18-dihydroxyoctadecanoate (902 in FIG. 9B), methyl 9,16-dihydroxyhexadecanoate (904 in FIG. 9C), methyl 9,18-dihydroxyhexadecanoate (906 in FIG. 9D), methyl 9,10,16-trihydroxyhexadecanoate (908 in FIG. 9E), methyl 9,10,18-trihydroxyoctadecanoate (910 in FIG. 9F), methyl 9,10-epoxy-16-hydroxyhexadecanoate (912 in FIG. 9G), and/or methyl 9,10-epoxy-18-hydroxyoctadecanoate (914 in FIG. 9H). Or, using glycerol as the alcohol can result in the production of glyceryl esters (e.g., 1-glyceryl or 2-glyceryl esters). For example, 1-glyceryl esters that can be produced include 2,3-dihydroxypropyl 10,16-dihydroxyhexadecanoate (1000 in FIG. 10A), 2,3-dihydroxypropyl 10,18-dihydroxyoctadecanoate (1002 in FIG. 10B), 2,3-dihydroxypropyl 9,16-dihydroxyhexadecanoate (1004 in FIG. 10C), 2,3-dihydroxypropyl 9,18-dihydroxyhexadecanoate (1006 in FIG. 10D), 2,3-dihydroxypropyl 9,10,16-trihydroxyhexadecanoate (1008 in FIG. 10E), 2,3-dihydroxypropyl 9,10,18-trihydroxyoctadecanoate (1010 in FIG. 10F), 2,3-dihydroxypropyl 9,10-epoxy-16-hydroxyhexadecanoate (1012 in FIG. 10G), and/or 2,3-dihydroxypropyl 9,10-epoxy-18-hydroxyoctadecanoate (1014 in FIG. 10H). 2-glyceryl esters that can be produced include 1,3-dihydroxypropan-2-yl 10,16-dihydroxyhexadecanoate (1100 in FIG. 11A), 1,3-dihydroxypropan-2-yl 10,18-dihydroxyoctadecanoate (1102 in FIG. 11B), 1,3-dihydroxypropan-2-yl 9,16-dihydroxyhexadecanoate (1104 in FIG. 11C), 1,3-dihydroxypropan-2-yl 9,18-dihydroxyhexadecanoate (1106 in FIG. 11D), 1,3-dihydroxypropan-2-yl 9,10,16-trihydroxyhexadecanoate (1108 in FIG. 11E), 1,3-dihydroxypropan-2-yl 9,10,18-trihydroxyoctadecanoate (1110 in FIG. 11F), 1,3-dihydroxypropan-2-yl 9,10-epoxy-16-hydroxyhexadecanoate (1112 in FIG. 11G), and/or 1,3-dihydroxypropan-2-yl 9,10-epoxy-18-hydroxyoctadecanoate (1114 in FIG. 11H).

In general, the method 300 in FIG. 3 can produce one or more compounds of Formula I:

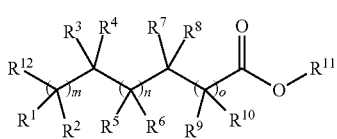

(Formula I)

wherein:
$R^1$, $R^2$, $R^3$, $R^4$, $R^5$, $R^6$, $R^7$, $R^8$, $R^9$, and $R^{10}$ are each independently —H, —$OR^{13}$, —$NR^{13}R^{14}$, —$SR^{13}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{13}$ and $R^{14}$ are each independently —H, —$C_1$-$C_6$ alkyl, —$C_1$-$C_6$ alkenyl, or —$C_1$-$C_6$ alkynyl;

$R^{11}$ is —H, -glyceryl, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{12}$ is —OH, —H, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^1$; and m, n, and o are each independently an integer in the range of 0 to 30, and $0 \leq m+n+o \leq 30$.

In some implementations, $R^1$, $R^2$, $R^3$, $R^4$, $R^5$, $R^6$, $R^8$, $R^9$, $R^{10}$, and $R^{12}$ in Formula I are each H. Additionally, the method 300 in FIG. 3 can produce one or more compounds of Formula II:

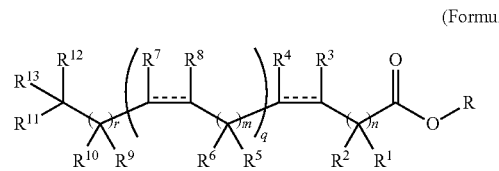

(Formula II)

wherein:
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —$C_1$-$C_6$ alkyl, —$C_2$-$C_6$ alkenyl, or —$C_2$-$C_6$ alkynyl;

the symbol ══ represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8; and

R is selected from —H, —$C_1$-$C_6$ alkyl, —$C_2$-$C_6$ alkenyl, —$C_2$-$C_6$ alkynyl, —$C_3$-$C_7$ cycloalkyl, aryl, 1-glyceryl, 2-glyceryl, or heteroaryl.

In some implementations, R is selected from —H, —CH₃, or —CH₂CH₃. The method 300 described herein can be used to produce one or more of the following methyl ester compounds:
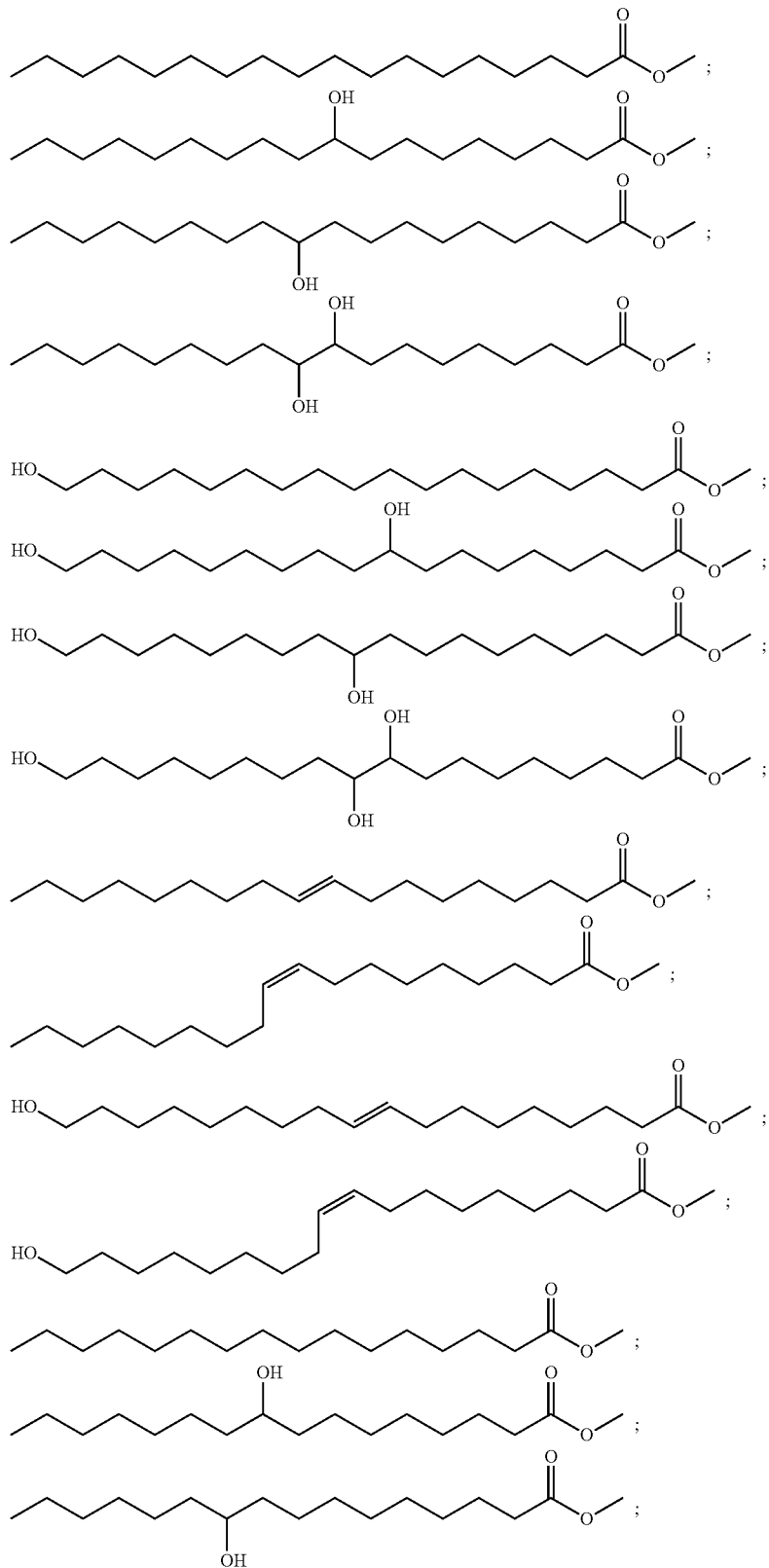

-continued
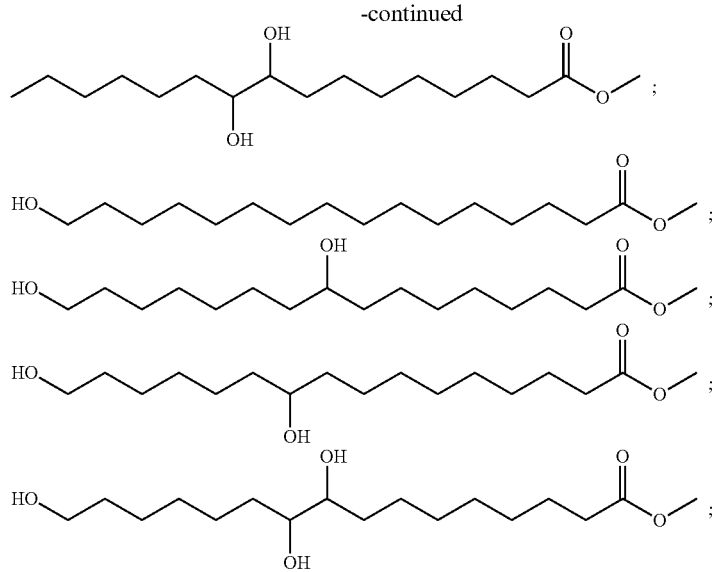
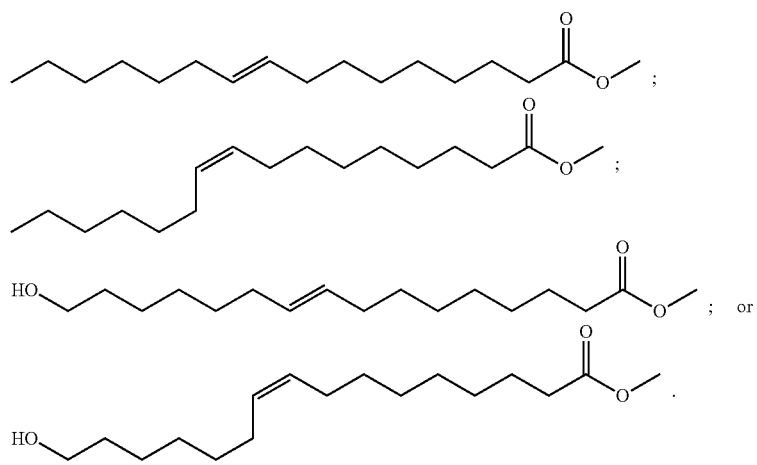
The method 300 described herein can also be used to produce one or more of the following ethyl ester compounds:
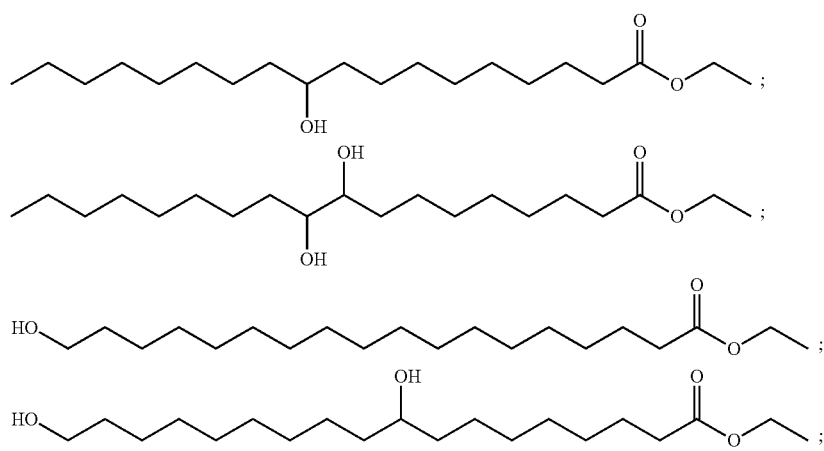

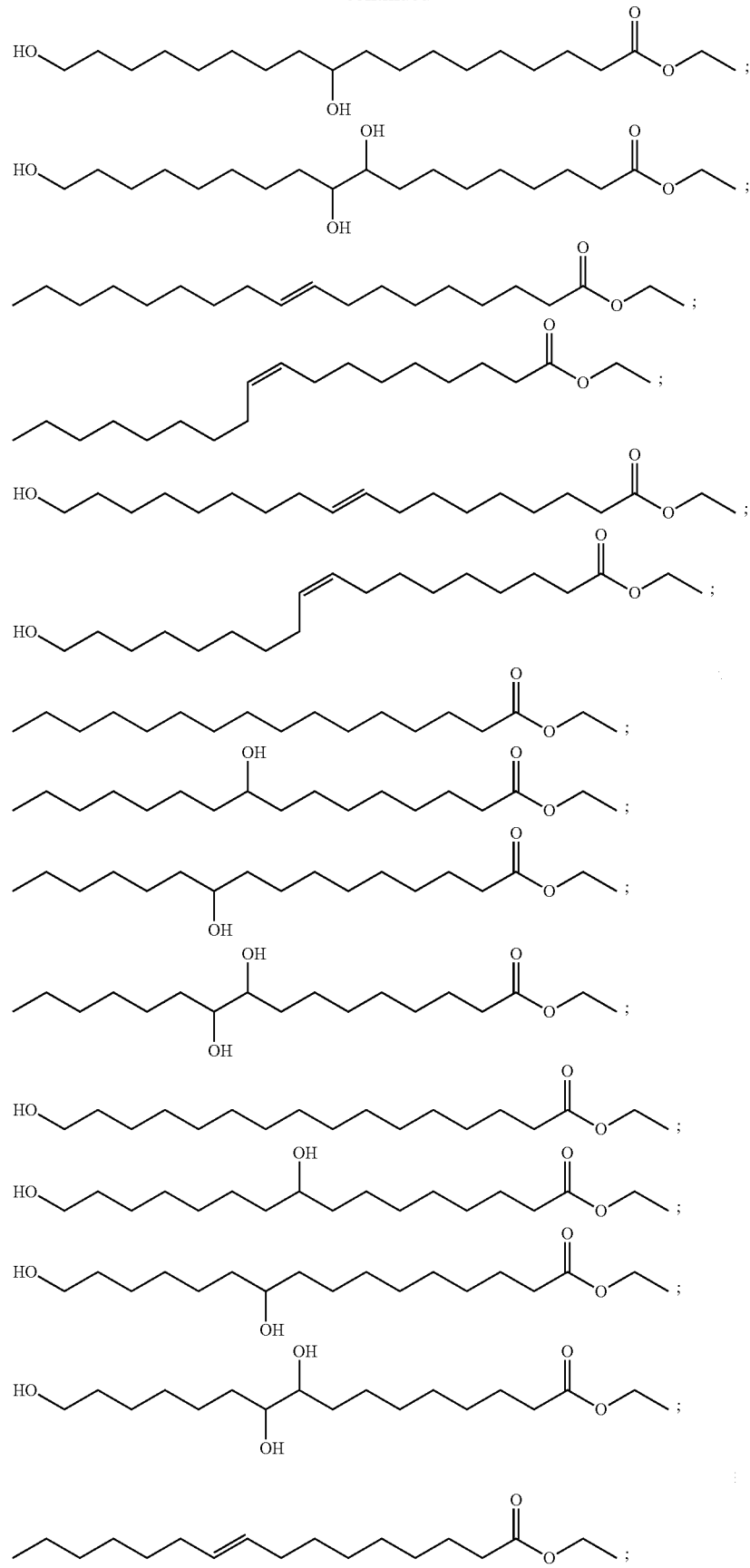

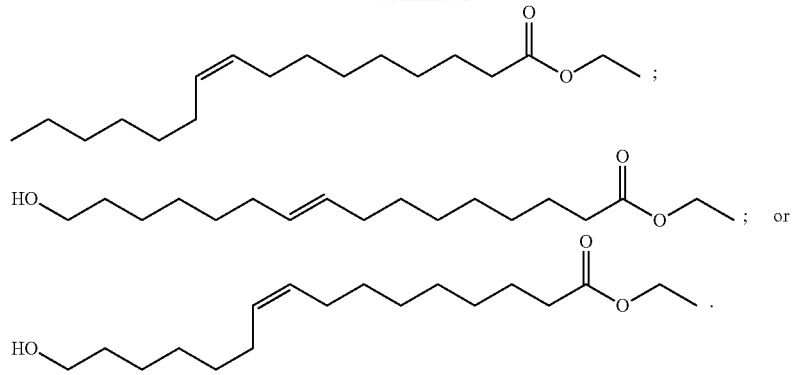
The method 300 described herein can also be used to produce one or more of the following 2-glyceryl ester compounds:
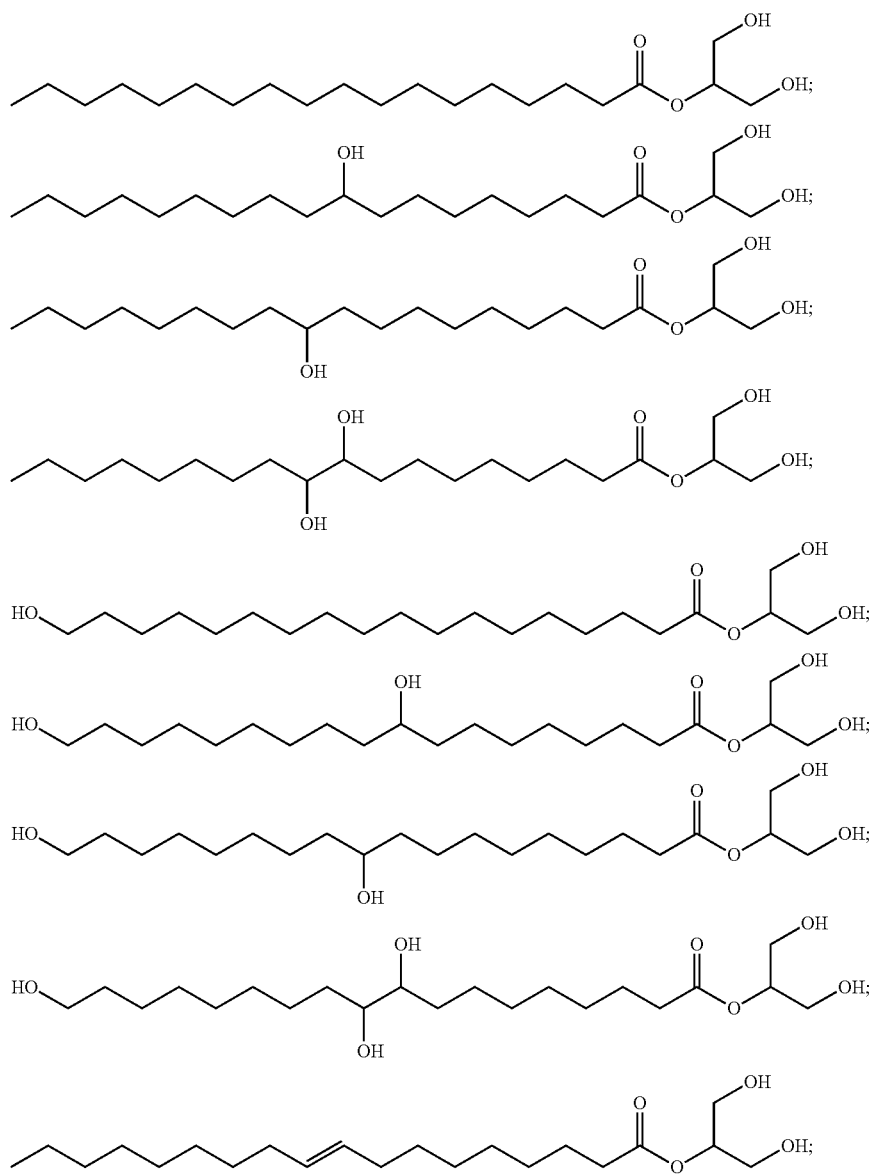

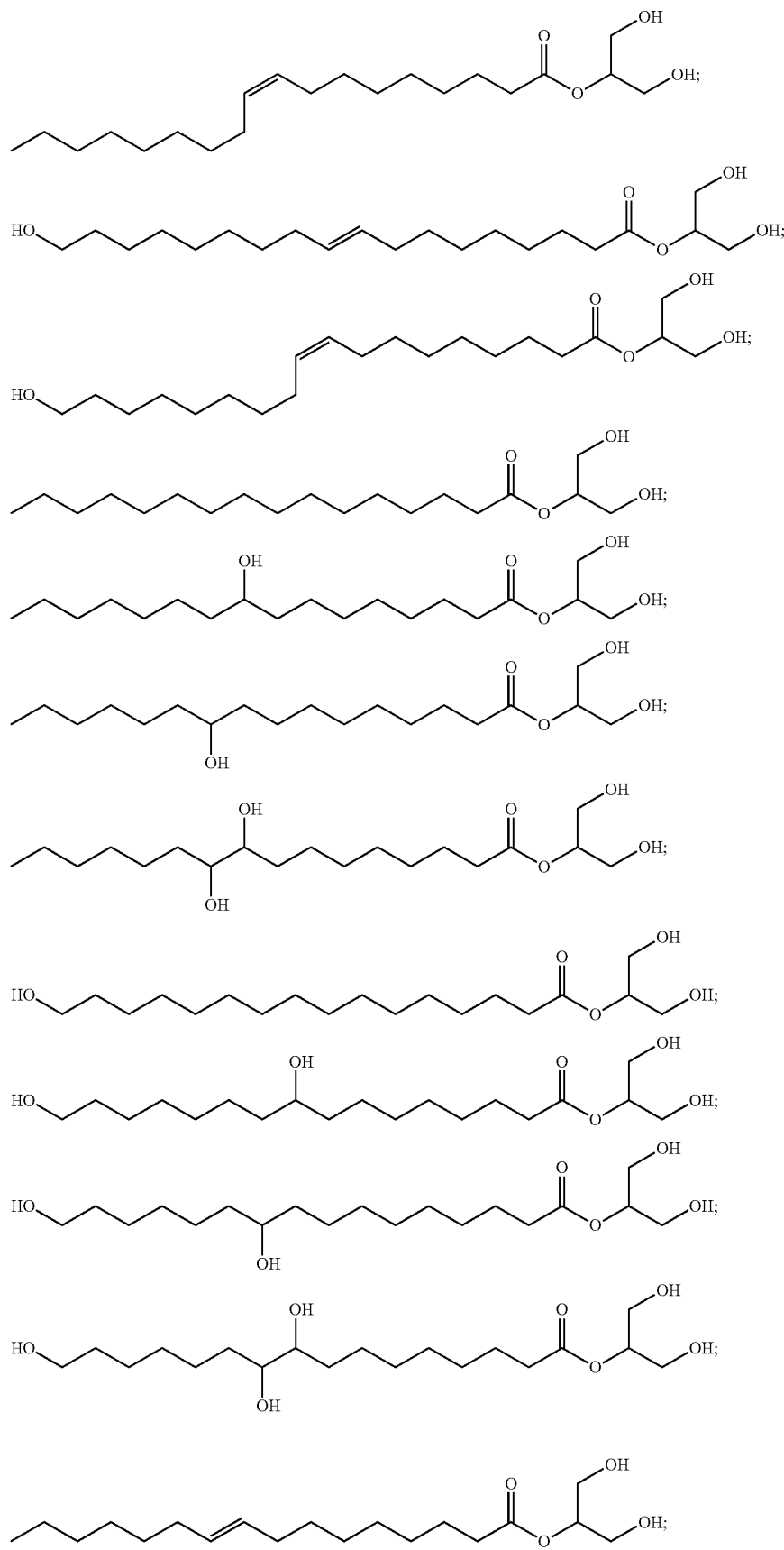

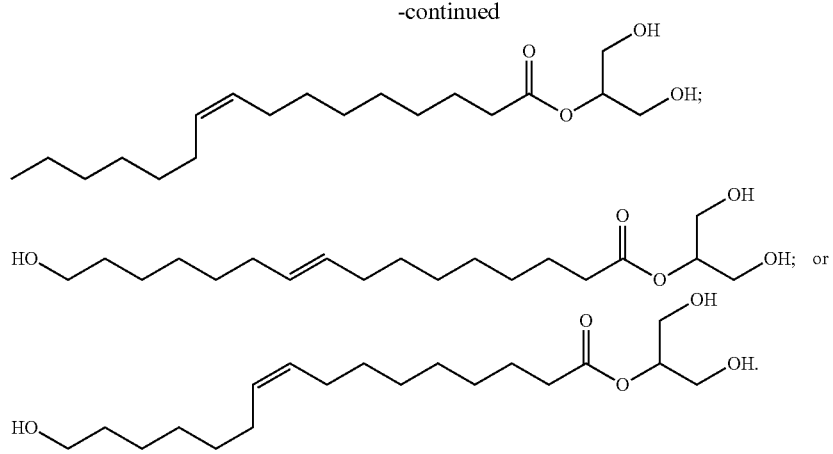
The method 300 described herein can also be used to produce one or more of the following 1-glyceryl ester compounds:
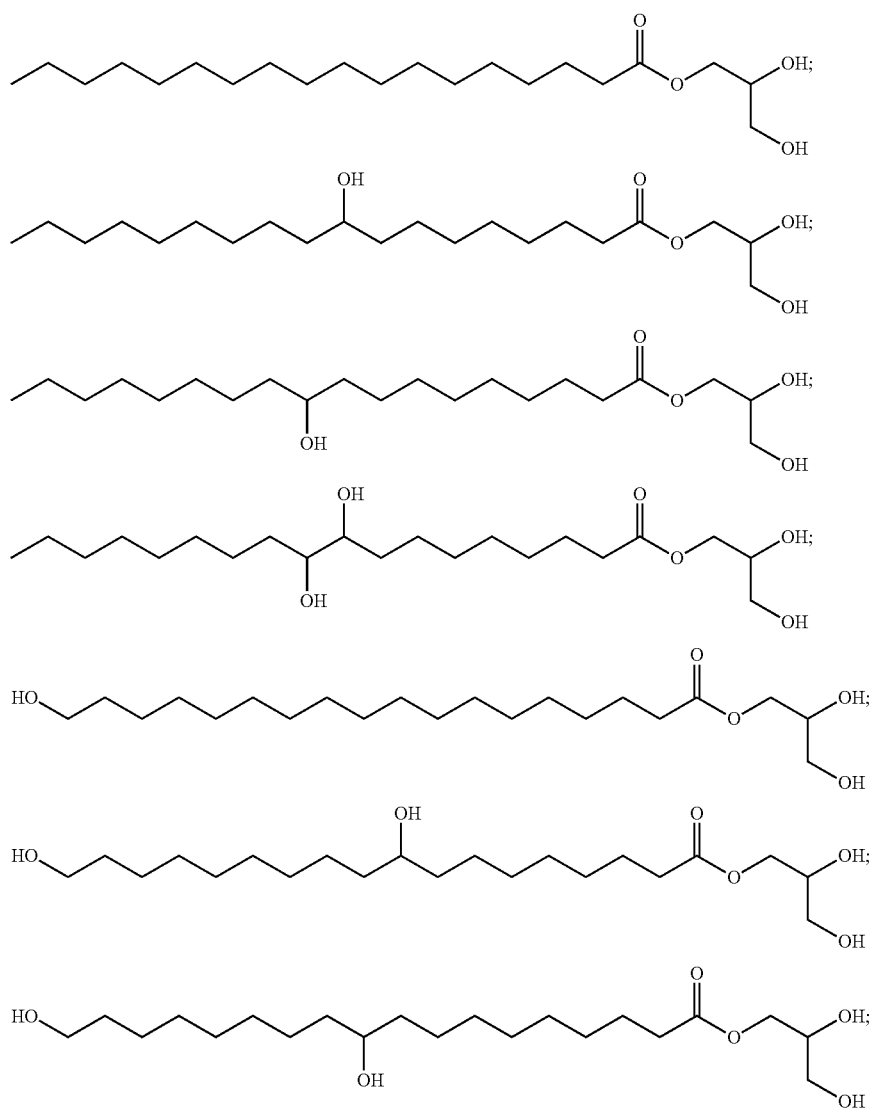

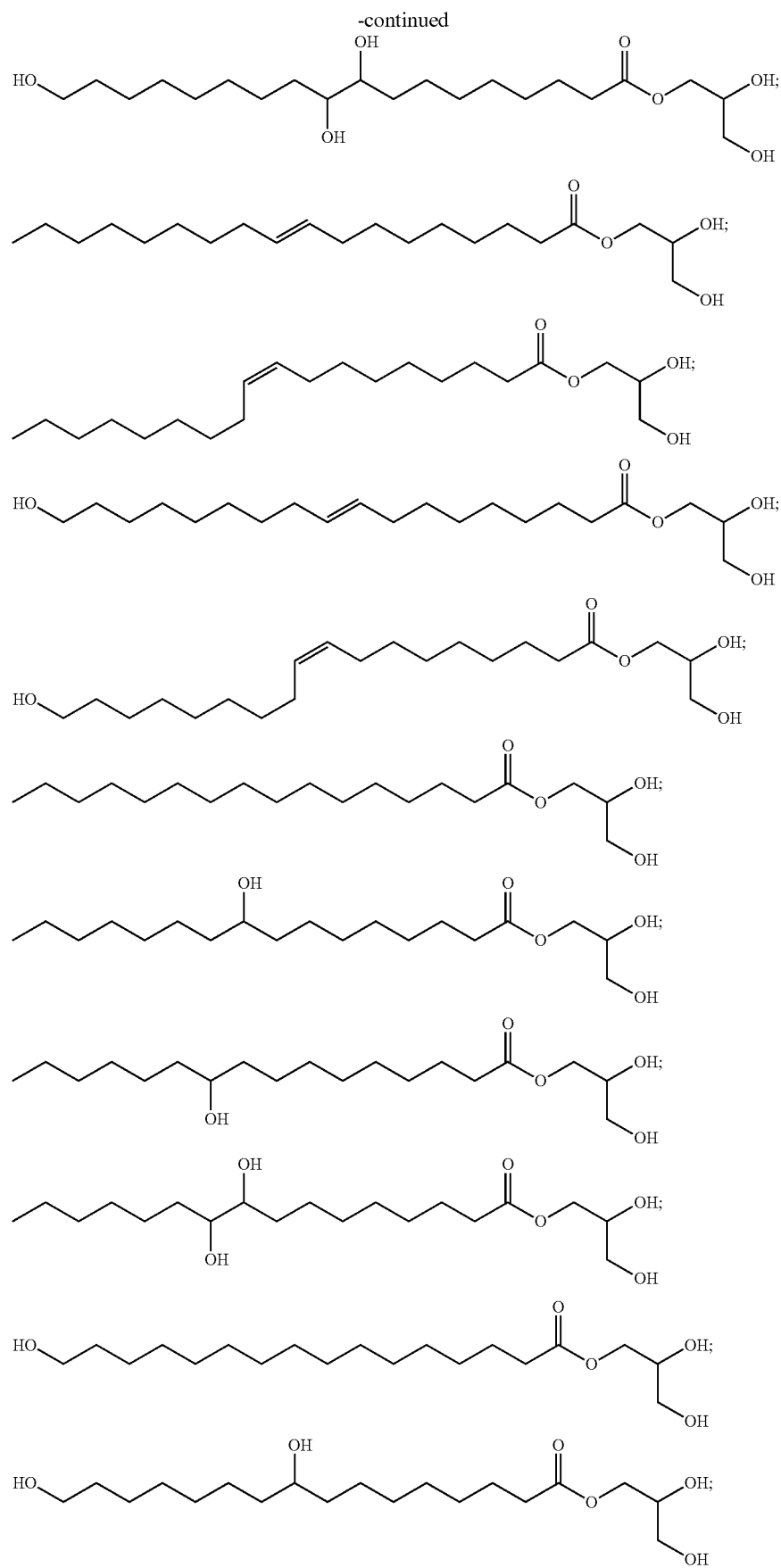

-continued

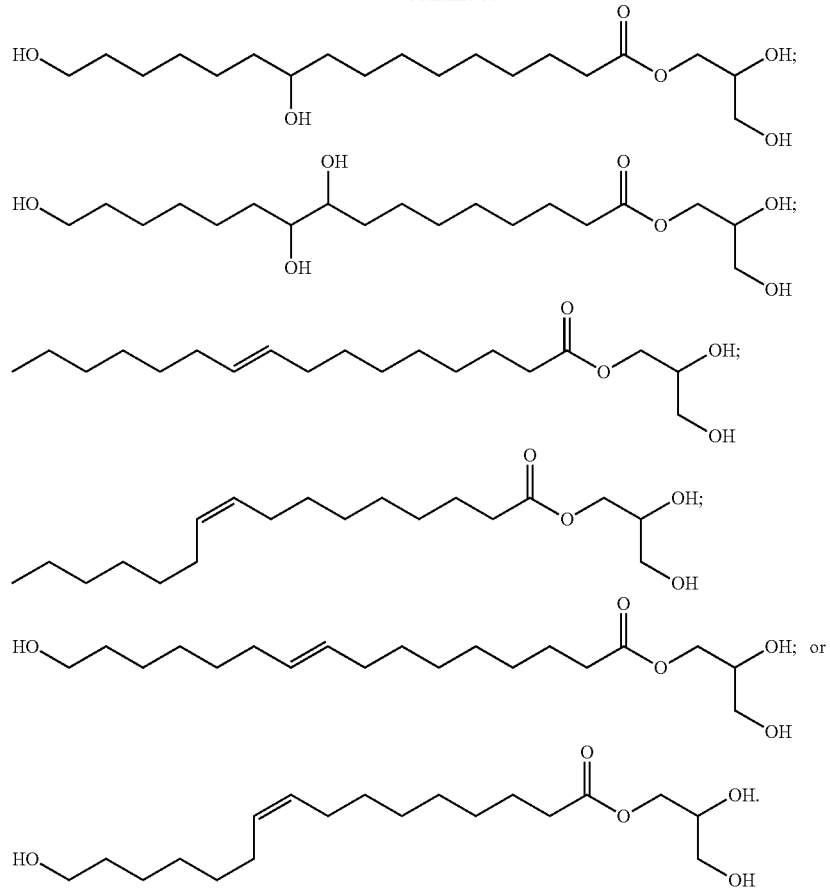

In some embodiments, the acid included in the solution used to depolymerize the crosslinked polyester is a strong acid. As used herein, a "strong acid" is one for which substantially all of the acid ionizes (dissociates) in a solution (provided there is sufficient solvent). A strong acid has a pKa<−1.74.

In some embodiments, the polyester, the acid, and the alcohol are heated in a sealed vessel above the atmospheric boiling point of the alcohol. This sealed vessel can allow higher temperatures to be reached, which can allow for shorter reaction times and/or less acid needed to obtain the product.

The fatty acid esters obtained by way of method 300 can be used in a variety of applications. For example, they can be applied directly to a plant or other agricultural product to form a protective coating, as further described below. Or, the esters may serve as starting material for further chemical transformations, for example for the production of free fatty acids. Although free fatty acids can be extracted from crosslinked polymers such as cutin using other methods (e.g., using method 100 of FIG. 1), forming free fatty acids via transesterification of esters obtained by way of method 300 can result in more highly purified product. For example, when methods 100 and 300 are each used to depolymerize cutin, the resulting crude extract in both cases is an oil. However, purification of the extract obtained by method 300 results in product which is a solid powder with little or substantially no coloration, and when dissolved in a solvent produces a solution with a low viscosity. On the other hand, purification of the extract obtained by method 100 results in product which remains oily with substantial coloration, and when dissolved in a solvent produces a solution with a substantially higher viscosity.

In some embodiments, the plant extract composition can be applied directly to a portion of a plant, e.g., to form a protective coating on the plant. In some embodiments, the plant extract composition can be heated to modify the physical and/or chemical properties of the composition prior to and/or during and/or after the application process. In some embodiments, the plant extract composition can be dissolved and/or suspended in a solvent, in aqueous solutions, or in a carrier liquid to form the coating. The solvent can include any polar, non-polar, protic, or aprotic solvents, including any combinations thereof. Examples of solvents that can be used to dissolve the plant extract compositions described herein include water, methanol, ethanol, isopropanol, butanol, acetone, ethyl acetate, chloroform, acetonitrile, tetrahydrofuran, diethyl ether, methyl tert-butyl ether, any other suitable solvent or a combination thereof. Aqueous solutions, suspensions, or emulsions of such plant extract compositions can be suitable for coating on agricultural products, for example, forming a coating on the agricultural product. For example, the aqueous solutions, suspensions, or emulsions can be applied to the surface of the agricultural product, after which the solvent can be removed (e.g., by evaporation or convective drying), leaving a protective coating formed from the plant extract composition on the surface of the agricultural product.

In some embodiments, the coatings can be configured to change the surface energy of the agricultural product. Various properties of coatings described herein can be adjusted by tuning the crosslink density of the coating, its thickness, or its composition. This can, for example, be used to control the ripening of postharvest fruit or produce. For example, coatings formed of plant extract compositions that primarily include bifunctional or polyfunctional cutin monomer units can, for example, have higher crosslink densities than those that include monofunctional cutin monomer units. Thus, plant extract composition coatings formed from bifunctional or polyfunctional cutin monomer units can in some cases result in slower rates of ripening as compared to coatings formed from monofunctional monomer units.

In some embodiments, an acid or a base can be added to the coating formulation to achieve a desired pH suitable for coating the agricultural product with the plant extract composition coating. In some embodiments, additives such as, for example, surfactants, emulsifiers, thickening agents, nonionic polymers, waxes, or salts can be included in the coating formulation. In some embodiments, weak acids, ions, or non-reactive molecules can be included in the coating formulation to control or adjust the properties of the resulting films or coatings. In some embodiments, pH stabilizers or modifiers can also be included in the coating formulation. In some embodiments, the coating formulation can include additional materials that are also transported to the surface with the coating, or are deposited separately and are subsequently encapsulated by the coating (e.g., the coating is formed at least partially around the additional material), or are deposited separately and are subsequently supported by the coating (e.g., the additional material is anchored to the external surface of the coating). Examples of such additional materials can include cells, biological signaling molecules, vitamins, minerals, pigments, aromas, enzymes, catalysts, antifungals, antimicrobials, and/or time-released drugs. The additional materials can be non-reactive with surface of the agricultural product and/or coating, or alternatively can be reactive with the surface and/or coating.

In some embodiments, the coating can include an additive configured, for example, to modify the viscosity, vapor pressure, surface tension, or solubility of the coating. In some embodiments, the additive can be configured to increase the chemical stability of the coating. For example, the additive can be an antioxidant configured to inhibit oxidation of the coating. In some embodiments the additive can be added to reduce or increase the melting temperature or the glass-transition temperature of the coating. In some embodiments, the additive can be configured to reduce the diffusivity of water vapor, oxygen, $CO_2$, or ethylene through the coating or enable the coating to absorb more ultra violet (UV) light, for example to protect the agricultural product (e.g., any of the products described herein). In some embodiments, the additive can be configured to provide an intentional odor, for example a fragrance (e.g., smell of flowers, fruits, plants, freshness, scents, etc.). In some embodiments, the additive can be configured to provide color and can include, for example, a dye or a US Food and Drug Administration (FDA) approved color additive. In some embodiments, the additives can include sweeteners, color additives, flavors, spices, flavor enhancers, fat replacers, and components of formulations used to replace fats, nutrients, emulsifiers, bulking agents, cleansing agents, stabilizers, emulsion stabilizers, thickeners, flavor or fragrance, an ingredient of a flavor or fragrance, binders, texturizers, humectants, pH control agents, acidulants, leavening agents, anti-caking agents, antifungal agents, antimicrobial agents, antioxidants, and/or UV filters. In some embodiments, the coating can include a photoinitiator, which can initiate crosslinking of the coating on exposure to an appropriate light source, for example, UV light.

In some embodiments, any of the plant extract composition coatings described herein can be flavorless or have high flavor thresholds, e.g. above 500 ppm, and can be odorless or have a high odor threshold. In some embodiments, the materials included in any of the coatings described herein can be substantially transparent. For example, the plant extract composition, the solvent, and/or any other additives included in the coating can be selected so that they have substantially the same or similar indices of refraction. By matching their indices of refraction, they may be optically matched to reduce light scattering and improve light transmission. For example, by utilizing materials that have similar indices of refraction and have a clear, transparent property, a coating having substantially transparent characteristics can be formed.

Any of the coatings described herein can be disposed on the external surface of an agricultural product using any suitable means. For example, in some embodiments, the agricultural product can be dip-coated in a bath of the coating formulation (e.g., an aqueous or mixed aqueous-organic or organic solution of the plant extract composition). The deposited coating can form a thin layer on the surface of an agricultural product, which can protect the agricultural product from biotic stressors, water loss, and/or oxidation. In some embodiments, the deposited coating can have a thickness of less than about 1500 nm, such that the coating is transparent to the naked eye. For example, the deposited coating can have a thickness of about 10 nm, about 20 nm, about 30 nm, about 40 nm, about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, 1,000 nm, about 1,100 nm, about 1,200 nm, about 1,300 nm, about 1,400 nm, or about 1,500 nm, inclusive of all ranges therebetween. In some embodiments, the deposited coating can be uniformly deposited over the agricultural product and free of defects and/or pinholes. In some embodiments, the dip-coating process can include sequential coating of the agricultural product in baths of coating precursors that can undergo self-assembly or covalent bonding on the agricultural product to form the coating. In some embodiments, the coating can be deposited on agricultural products by passing the agricultural products under a stream of the coating formulation (e.g., a waterfall of the liquid coating). For example, the agricultural products can be disposed on a conveyor that passes through the stream of the coating formulation. In some embodiments, the coating can be misted, vapor- or dry vapor-deposited on the surface of the agricultural product. In some embodiments, the coating can be configured to be fixed on the surface of the agricultural product by UV crosslinking or by exposure to a reactive gas, for example, oxygen.

In some embodiments, the plant extract composition coating can be spray-coated on the agricultural products. Commercially available sprayers can be used for spraying the coating or precursors of the coating onto the agricultural product. In some embodiments, the coating formulation can be electrically charged in the sprayer before spray-coating on to the agricultural product, such that the deposited coating electrostatically and/or covalently bonds to the exterior surface of the agricultural product.

The coatings formed from plant extract compositions described herein can be configured to prevent water loss or other moisture loss from the coated portion of the plant, delay ripening, and/or prevent oxygen diffusion into the coated portion of the plant, for example, to reduce oxidation of the coated portion of the plant. The coating can also protect the coated portion of the plant against biotic stressors, such as, for example, bacteria, fungi, viruses, and/or pests that can infest and decompose the coated portion of the plant. Since bacteria, fungi and pests all identify food sources via recognition of specific molecules on the surface of the agricultural product, coating the agricultural products with the coating containing the plant extract compositions can deposit molecularly contrasting molecules on the surface of the portion of the plant, which can render the agricultural products unrecognizable. Furthermore, the coating can also alter the physical and/or chemical environment of the surface of the agricultural product making the surface unfavorable for bacteria, fungi or pests to grow. The coating can also be formulated to protect the surface of the portion of the plant from abrasion, bruising, or otherwise mechanical damage, and/or protect the portion of the plant from photodegradation. The portion of the plant can include, for example, a leaf, a stem, a shoot, a flower, a fruit, a root, etc. In some embodiments, the coating can be used to coat fruits and, for example, delay ripening of the fruit.

Any of the coatings described herein can be disposed on the external surface of an agricultural product using any suitable means. For example, in some embodiments, the agricultural product can be dip coated in a bath of the coating composition (e.g., an aqueous solution of hydrogen-bonding organic molecules). The coating can form a thin layer on the surface of agricultural product, which can protect the agricultural product from biotic stressors, water loss, and/or oxidation. In some embodiments, the deposited coating can have a thickness of less than about 2 microns, for example less than 1 micron, less than 900 nm, less than 800 nm, less than 700 nm, less than 600 nm, less than 500 nm, less than 400 nm, less than 300 nm, less than 200 nm, or less than 100 nm, such that the coating is transparent to the naked eye. For example, the deposited coating can have a thickness of about 50 nm, 60 nm, 70 nm, 80 nm, 90 nm, 100 nm, 110 nm, 120 nm, 130 nm, 140 nm, 150 nm, 200 nm, 250 nm, 300 nm, 350 nm, 400 nm, 450 nm, 500 nm, 600 nm, 700 nm, 800 nm, 900 nm, or about 1,000 nm inclusive of all ranges therebetween. The deposited coating can have a high degree of crystallinity to decrease permeability, such that the coating is conformally deposited over the agricultural product and is free of defects and/or pinholes. In some embodiments, the dip coating process can include sequential coating of the agricultural product in baths of precursors that can undergo self-assembly or covalent bonding on the agricultural product to form the coating. In some embodiments, the coatings can be deposited on agricultural products by passing the agricultural products under a stream of the coating (e.g., a waterfall of the liquid coating). For example, the agricultural products can be disposed on a conveyor that passes through the stream of the coating. In some embodiments, the coating can be vapor deposited on the surface of the agricultural product. In some embodiments, the coating can be formulated to be fixed on the surface of the agricultural product by UV cross-linking or by exposure to a reactive gas, for example, oxygen. In some embodiments, the coating can be applied in the field before harvest as an alternative to pesticides.

In some embodiments, the fatty acid esters and/or oligomers thereof are dissolved in a suitable solvent (e.g., water, ethanol, or a combination thereof) prior to coating the agricultural product. In some embodiments the process of disposing the composition on the agricultural product comprises dip-coating the agricultural product in a solution comprising the plurality of cutin-derived monomers, oligomers, or combinations thereof. In some embodiments the process of disposing the composition on the agricultural product comprises spray-coating the produce with a solution comprising the plurality of fatty acid esters and/or oligomers thereof.

In some embodiments, any of the coatings can be spray coated on the agricultural products. Commercially available sprayers can be used for spraying the coating or precursors of the coating onto the agricultural product. In some embodiments, the coatings can be electrically charged in the sprayer before spray coating on the agricultural product, such that the coating covalently bonds to the exterior surface of the agricultural product.

In some embodiments, the coating can be deposited on the agricultural product such that the coating is unbound to the surface of the agricultural product. In some embodiments, one or more components of the coating, for example, the hydrogen-bonding organic molecule, can be covalently (or hydrogen) bonded to at least a portion of the surface of the agricultural product. This can result in improved coating properties such as, for example, higher durability, tighter control of coating permeability and thickness. In some embodiments, multiple layers of the coating can be deposited on the surface of agricultural product to achieve a durable coating.

Any of the coatings described herein can be used to protect any agricultural product. In some embodiments, the coating can be coated on an edible agricultural product, for example, fruits, vegetables, edible seeds and nuts, herbs, spices, produce, meat, eggs, dairy products, seafood, grains, or any other consumable item. In such embodiments, the coating can include components that are non-toxic and safe for consumption by humans and/or animals. For example, the coating can include components that are U.S. Food and Drug Administration (FDA) approved direct or indirect food additives, FDA approved food contact substances, satisfy FDA regulatory requirements to be used as a food additive or food contact substance, and/or is an FDA Generally Recognized as Safe (GRAS) material. Examples of such materials can be found within the FDA Code of Federal Regulations Title 21, located at "http://www.accessdata.fda.gov/scripts/cdrh/cfdocs/cfcfr/cfrsearch.cfm", the entire contents of which are hereby incorporated by reference herein. In some embodiments, the components of the coating can include a dietary supplement or ingredient of a dietary supplement. The components of the coating can also include an FDA approved food additive or color additive. In some embodiments, the coating can include components that are naturally derived, as described herein. In some embodiments, the coating can be flavorless or have a high flavor threshold of below 500 ppm, are odorless or have a high odor threshold, and/or are substantially transparent. In some embodiments, the coating can be configured to be washed off an edible agricultural product, for example, with water.

In some embodiments, the coatings described herein can be formed on an inedible agricultural product. Such inedible agricultural products can include, for example, inedible flowers, seeds, shoots, stems, leaves, whole plants, and the like. In such embodiments, the coating can include components that are non-toxic, but the threshold level for non-toxicity can be higher than that prescribed for edible products. In such embodiments, the coating can include an FDA approved food contact substance, an FDA approved food additive, or an FDA approved drug ingredient, for example, any ingredient included in the FDA's database of approved drugs, which can be found at "http://www.accessdata.fda.gov/scripts/cder/drugsatfda/index.cfm", the entire contents of which are hereby incorporated herein by reference. In some embodiments, the coating can include materials that satisfy FDA requirements to be used in drugs or are listed within the FDA's National Drug Discovery Code Directory, "http://www.accessdata.fda.gov/scripts/cder/ndc/default.cfm", the entire contents of which are hereby incorporated herein by reference. In some embodiments, the materials can include inactive drug ingredients of an approved drug product as listed within the FDA's database, "http://www.accessdata.fda.gov/scripts/cder/ndc/default.cfm", the entire contents of which are hereby incorporated herein by reference.

Embodiments of the coatings described herein provide several advantages, including, for example: (1) the coatings can protect the agricultural products from biotic stressors, i.e. bacteria, viruses, fungi, or pests; (2) the coatings can prevent evaporation of water and/or diffusion of oxygen; (3) coating can help extend the shelf life of agricultural products, for example, postharvest produce, without refrigeration; (4) the coatings can introduce mechanical stability to the surface of the agricultural products eliminating the need for expensive packaging designed to prevent the types of bruising which accelerate spoilage; (5) use of agricultural waste materials to obtain the coatings can help eliminate the breeding environments of bacteria, fungi, and pests; (6) the coatings can be used in place of pesticides to protect plants, thereby minimizing the harmful impact of pesticides to human health and the environment; (7) the coatings can be naturally derived and hence, safe for human consumption. Since the components of the coatings described herein can in some embodiments be obtained from agricultural waste, such coatings can be made at a relatively low cost. Therefore, the coatings can be particularly suited for small scale farmers, for example, by reducing the cost required to protect crops from pesticides and reducing postharvest losses of agricultural products due to decomposition by biotic and/or environmental stressors.

In some embodiments, the treating of the crosslinked polymer and/or forming of the plant extract composition is carried out by a first party, while the application of the plant extract composition to an agricultural product to form a protective coating over the agricultural product is carried out by a second party different from the first party. For example, a manufacturer of the plant extract compositions (i.e., a first party) can form the compositions by one or more of the methods described herein. The manufacturer can then sell or otherwise provide the resulting plant extract composition to a second party, for example a farmer, shipper, distributor, or retailer of produce, and the second party can apply the composition to one or more agricultural products to form a protective coating over the products. Alternatively, the manufacturer can sell or otherwise provide the resulting plant extract composition to an intermediary party, for example a wholesaler, who then sells or otherwise provides the plant extract composition to a second party such as a farmer, shipper, distributor, or retailer of produce, and the second party can apply the composition to one or more agricultural products to form a protective coating over the products.

In some cases where multiple parties are involved, the first party may optionally provide instructions or recommendations about the extract composition, either written or oral, indicating one or more of the following: (i) that the composition is intended to be applied to a product for the purpose of coating or protecting the product, to extend the life of the product, to reduce spoilage of the product, or to modify or improve the aesthetic appearance of the product; (ii) conditions and/or methods that are suitable for applying the compositions to the surfaces of products; and/or (iii) potential benefits (e.g., extended shelf life, reduced rate of mass loss, reduced rate of molding and/or spoilage, etc.) that can result from the application of the composition to a product. While the instructions or recommendations may be supplied by the first party directly with the plant extract composition (e.g., on packaging in which the composition is sold or distributed), the instructions or recommendations may alternatively be supplied separately, for example on a website owned or controlled by the first party, or in advertising or marketing material provided by or on behalf of the first party.

In view of the above, it is recognized that in some cases, a party that manufactures a plant extract composition according to one or more methods described herein (i.e., a first party) may not directly form a coating over a product from the extract composition, but can instead direct (e.g., can instruct or request) a second party to form a coating over a product from the extract composition. That is, even if the first party does not coat a product by the methods and compositions described herein, the first party may still cause the plant extract composition to be applied to the product to form a protective coating over the product by providing instructions or recommendations as described above. Accordingly, as used herein, the act of applying a plant extract composition to a product (e.g., a plant or agricultural product) also includes directing or instructing another party to apply the plant extract composition to the product, or causing the plant extract composition to be applied to the product.

The following examples describe plant extract compositions and methods for obtaining the same. These examples are only for illustrative purposes and are not meant to limit the scope of the present disclosure.

EXAMPLES

In each of the examples below, all reagents and solvents were purchased and used without further purification unless specified. All reactions were carried out under an atmosphere of nitrogen with commercial grade solvents unless otherwise stated. Reactions were monitored by thin layer chromatography (TLC) carried out on 0.25 mm E. Merck silica gel plates (60 Å, F-254) using UV light as the visualizing agent and an acidic mixture of anisaldehyde, ceric ammonium molybdate, or basic aqueous potassium permanganate ($KMnO_4$), and heat as developing agents. NMR spectra were recorded on a Bruker Avance 500 MHz and/or Varian VNMRs 600 MHz instruments and calibrated using residual un-deuterated solvent as an internal reference (eg. $CHCl_3$@ 7.26 ppm $^1H$ NMR, 77.16 ppm $^{13}C$ NMR). The following abbreviations (or combinations thereof) were used to explain the multiplicities: s=singlet, d=doublet, t=triplet, q=quartet, m=multiplet, br=broad. Mass spectra (MS) were recorded on a Waters Xevo UPLC equipped with a Cis column and a ESI TQD MS. Absolute ethanol was dried to low residual water according to the procedures in Purification of Laboratory Chemicals ($7^{th}$ ed.)

Example 1: Method for Preparing Tomato Pomace Prior to Depolymerization

Tomato pomace obtained from a commercial tomato processing facility was milled in a cutting mill, and sifted to give different particle size distributions (eg. >500 μm, 250-500 μm, 125-250 μm, etc.). The fraction corresponding to 250-500 μm was sequentially extracted with CHCl$_3$ overnight in a Soxhlet extractor and with methanol overnight in a Soxhlet extractor to remove the surface waxes and other soluble components, followed by drying under vacuum (<1 torr). The washed pomace was then lyophilized overnight (<0.02 torr) to remove water, and then stored in a desiccator before use.

Example 2: Method for Preparing a Composition from Tomato Skin/Peel Treated in a Base and an Alcohol A general procedure for base catalyzed depolymerization is as follows. To depolymerize the dried and washed pomace, an ethanolic solution including a stoichiometric excess (relative to tomato pomace) of sodium ethoxide was prepared in an oven dried three neck round bottom by adding 2 eq. sodium metal (rel. to tomato pomace, assuming that the mass is entirely composed of cutin polymer) to 250 mL anhydrous ethanol under a nitrogen atmosphere. The mixture was stirred under nitrogen until the sodium had completely dissolved, after which 10.0 g of the tomato pomace (250-500 m in size) was added against a counter-flow of nitrogen. The mixture was refluxed under nitrogen for 48 hours, followed by cooling the reaction to room temperature and quenching it with 3 mL glacial acetic acid to a pH of about 7. The resulting solution was filtered using Grade 1 Whatman filter paper to remove any leftover solids and the filtrate was collected. Any excess solvent was removed from the filtered solution by rotary evaporation. The crude isolate was dried under high vacuum (<0.1 torr), and was analyzed by UPLC and NMR. The crude isolate was found to contain (9)10,16-dihydroxypalmitic acid, with no evidence of ethyl ester formation.

Example 3: Method for Preparing a Composition from Tomato Skin/Peel Treated in an Acid and an Alcohol To 250 mL of absolute ethanol was added sulfuric acid (7.36 g, 4.00 mL, 75.0 mmol) and tomato pomace (10.0 g, 500 μm-250 μm in size) with stirring. The reaction was then heated to reflux for 48 hours. Once complete, the reaction was cooled and the solution neutralized to pH 7 with ~70 mL sat. NaHCO$_3$(aq). The neutralized mixture was then filtered through a Buchner funnel and Grade 1 Whatman (70 mm) filter paper. The filtrate was dried by sequential rotary evaporation and high vacuum (<0.1 torr). When the crude material was dry, it was taken up in ethyl acetate (140 mL) and three forward extractions were conducted with H$_2$O (2×160 mL) and brine (160 mL). The organic layer was separated, and the combined aqueous phases were extracted with an additional 200 mL ethyl acetate, and the organic phases combined, and dried with MgSO$_4$. The solvent was removed with rotary evaporation and high vacuum, yielding 3.35 g (avg.) of crude isolate.

Figure 12:
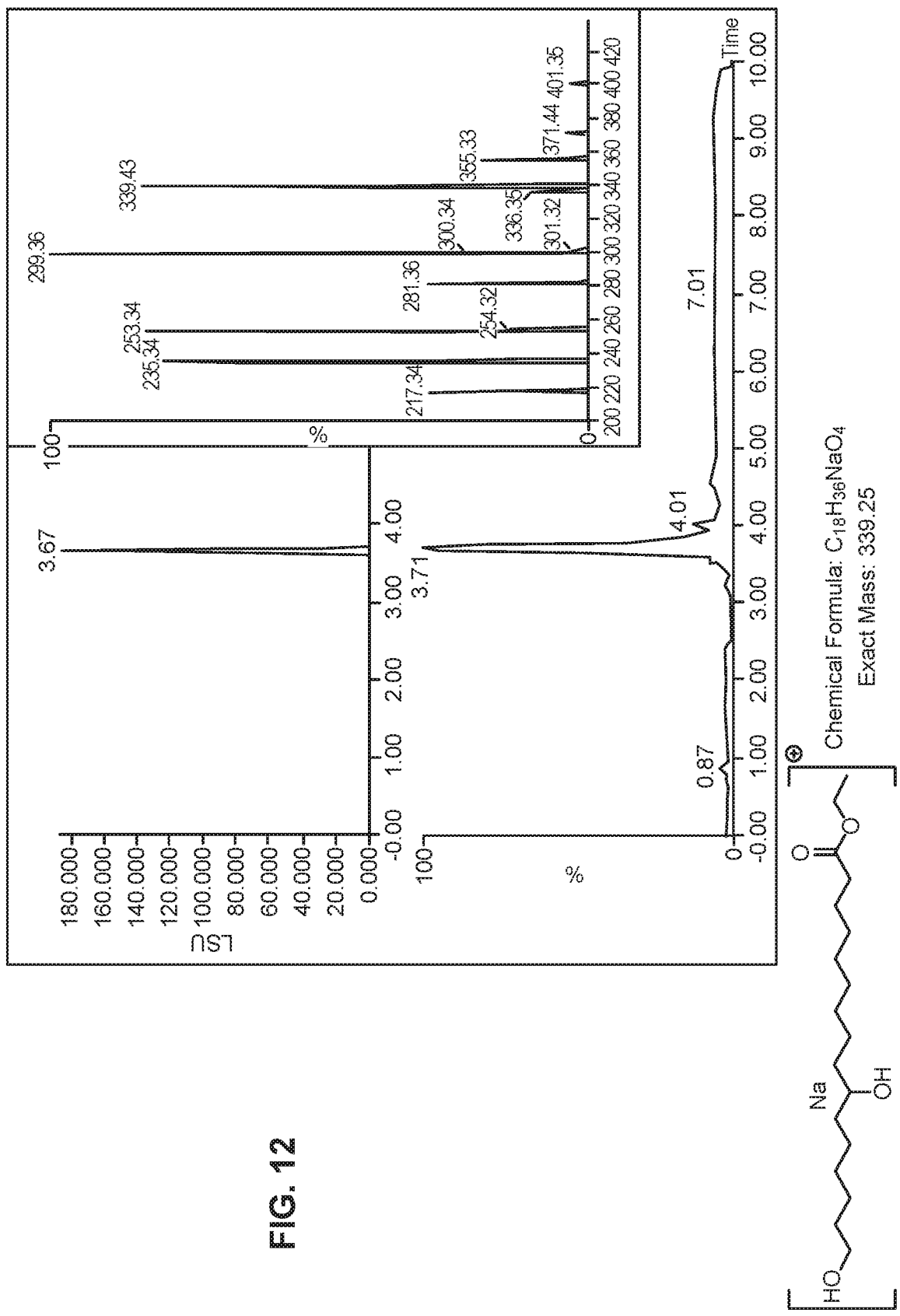
FIGS. 12 and 13 illustrate characterization of a composition prepared according to the method of FIG. 3.
Figure 13:
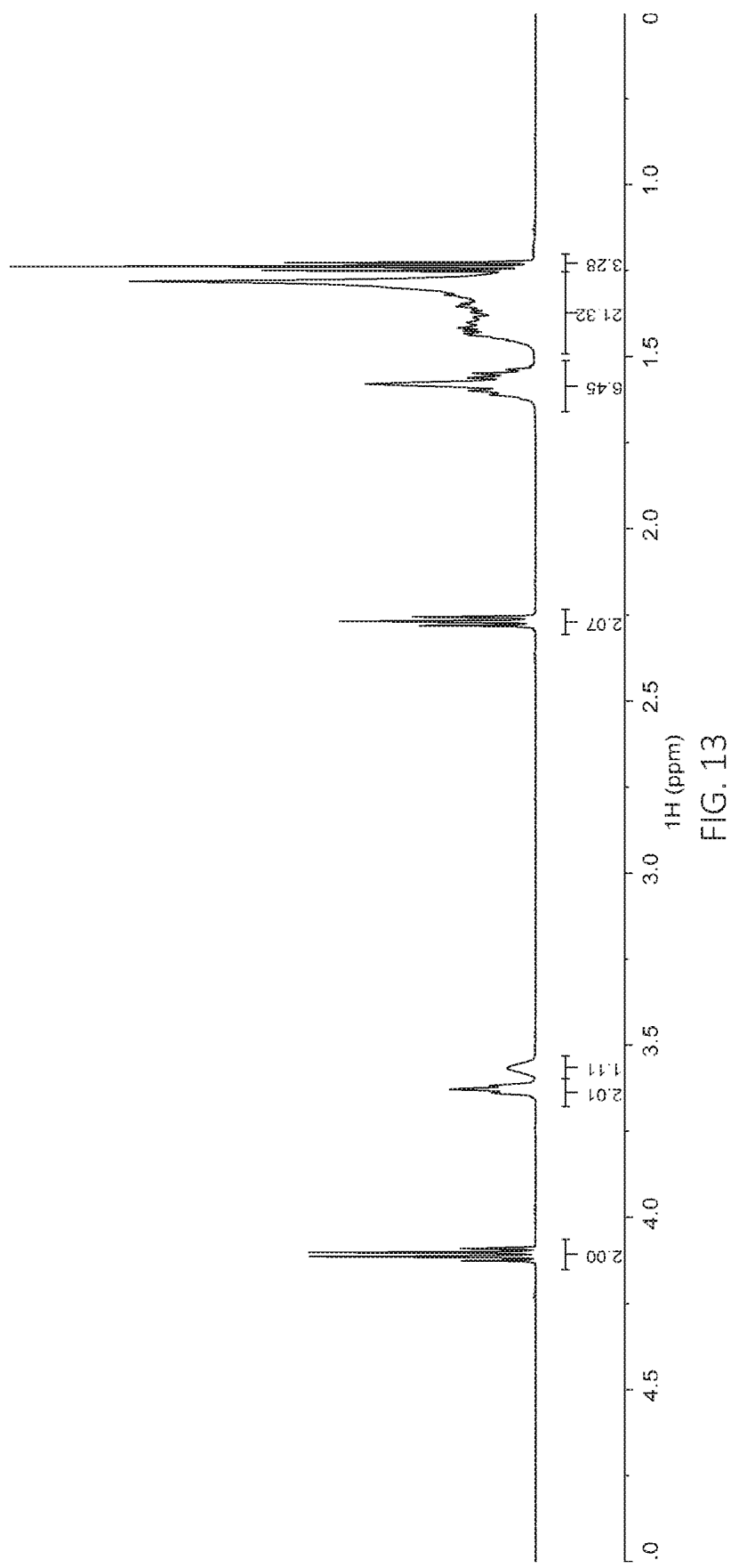
Figure 15:
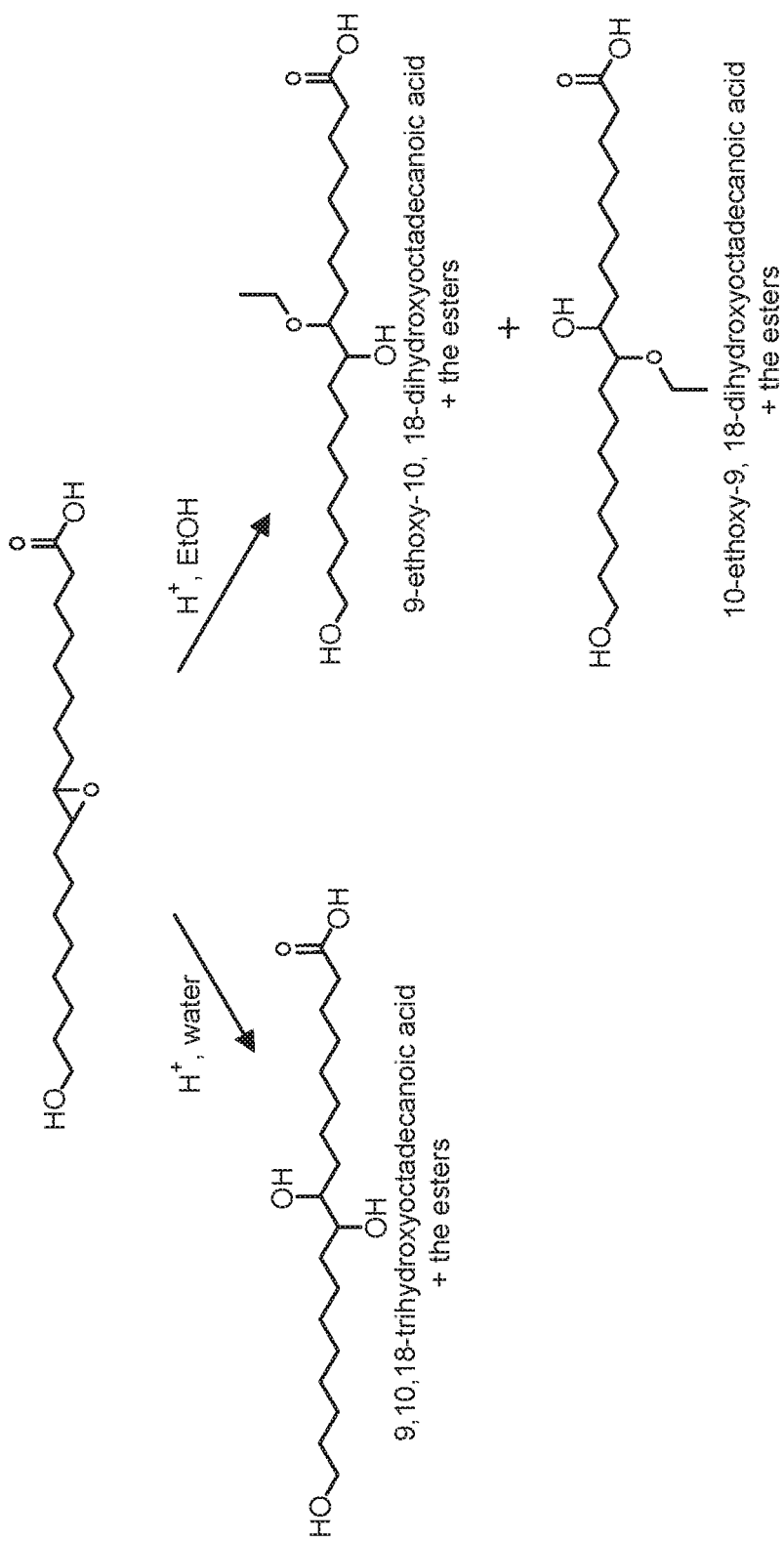
FIG. 15 depicts an epoxide ring-opening reaction. The products of epoxide ring-opening reactions may be treated according to the methods described herein for the purpose of coating and/or preserving fruits and vegetables.

The crude isolate from the ethanolysis was dissolved in methanol, and three times the mass of the crude isolate in Celite 545 was added. The methanol was removed by rotary evaporator and dried Celite admixture transferred to a cellulose extraction thimble. Glass wool was placed on top of the material to ensure it stayed in the thimble. The material was extracted in a Soxhlet extractor for 20 hours under nitrogen with 600 mL of heptane. After 20 hours, the Soxhlet apparatus and contents were cooled. The Soxhlet apparatus was then dismantled, and the round bottom was placed in a fumehood overnight, which allowed a first crop of ethyl 10,16-dihydroxyhexdecanoate (EtDHPA) to precipitate out of the heptane. The round bottom was then placed in a 2° C. fridge overnight, giving a second crop of EtDHPA. The second crop was then filtered and transferred to a scintillation vial. Both crops were dried by sequential treatment with a rotary evaporator and high vacuum (<0.1 torr), resulting in a yellowish (first crop)/white (second crop) powder. Both crops were analyzed by NMR and UPLC/ESI MS, matching the expected spectra for EtDHPA; yield (combined crops): 0.76 g. $^1$H NMR (600 MHz, Chloroform-d) δ 4.11 (q, J=7.1 Hz, 2H), 3.63 (t, J=6.8 Hz, 2H), 3.57 (s, 1H), 2.27 (t, J=7.6 Hz, 2H), 1.66-1.51 (m, 6H), 1.49-1.25 (m, 21H), 1.24 (t, J=7.1 Hz, 3H). See FIG. 12 (UPLC) and FIG. 13 (NMR).

Example 4: Method for Preparing a Composition from Tomato Skin/Peel Treated in an Acid and an Alcohol at High Temperatures To a thick-walled sealed tube containing 250 mL of absolute ethanol was added sulfuric acid (7.36 g, 4.00 mL, 75.0 mmol), followed by tomato pomace (10.0 g, 500 m-250 m in size). The reaction was then heated to temperatures greater than the atmospheric boiling point of ethanol, such as 100° C. or 120° C. for 24 or 48 hours. Once complete, the reaction was cooled and the solution neutralized to pH 7 with ~70 mL sat. NaHCO$_3$(aq.). The neutralized mixture was then filtered through a Buchner funnel and Grade 1 Whatman (70 mm) filter paper. The filtrate was dried by sequential rotary evaporation and high vacuum (<0.1 torr). When the crude material was dry, it was taken up in ethyl acetate (140 mL), and three forward extractions were conducted with H$_2$O (2×160 mL) and brine (160 mL). The organic layer was separated, and the combined aqueous phases were extracted with an additional 200 mL ethyl acetate, and the organic phases combined, and dried with MgSO$_4$. The solvent was removed with rotary evaporation and high vacuum, yielding the crude isolate. The amounts of crude recovered at each of the different temperature and time conditions are plotted in FIG. 5.

The crude isolate obtained from the ethanolysis was dissolved in methanol, and three times the mass of the crude isolate in Celite 545 was added. The methanol was removed by rotary evaporator and the dried Celite admixture transferred to a cellulose extraction thimble. Glass wool was placed on top of the material to ensure it stayed in the thimble. The material was extracted for 20 hours under nitrogen in a Soxhlet extractor with 500 mL of heptane and then cooled. The Soxhlet apparatus was then dismantled and the round bottom was placed in the fumehood overnight, which allowed a first crop of EtDHPA to precipitate out of the heptane. The round bottom was then placed in a 4° C. fridge overnight, providing a second crop of EtDHPA. This precipitate was then filtered and transferred to a scintillation vial. Both crops were dried by sequential treatment with a rotary evaporator and high vacuum (<0.1 torr) to give a white/yellowish powder. Both crops were analyzed by NMR and UPLC/ESI MS, matching the expected spectra for EtDHPA. The amounts recovered of the EtDHPA isolate are shown in FIGS. 5 and 6.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made. Accordingly, other implementations are within the scope of the following claims.

The invention claimed is:

1. A method of preparing a composition comprising fatty acid esters, the method comprising:
    providing a crosslinked polyester comprising polymerized mono- or polyhydroxy fatty acids;
    treating the crosslinked polyester with an acid and an alcohol at a temperature from 78° C. to 120° C., wherein the acid is combined with the alcohol in superstoichiometric amounts;
    removing the acid and the alcohol to form a mixture comprising the fatty acid esters; and
    purifying the mixture to isolate the fatty acid esters.

2. The method of claim 1, wherein the crosslinked polyester is naturally occurring.

3. The method of claim 1, wherein the crosslinked polyester is derived from plant matter.

4. The method of claim 1, wherein the crosslinked polyester is cutin.

5. The method of claim 4, wherein the cutin is derived from plant skins.

6. The method of claim 1, wherein the crosslinked polyester contains endogenous water.

7. The method of claim 6, wherein the method is characterized as only requiring a single step to obtain the mixture comprising the fatty acid esters from the crosslinked polyester.

8. The method of claim 1, wherein the alcohol comprises ethanol, methanol, propanol, glycerol, or isopropanol.

9. The method of claim 1, wherein removing the acid comprises neutralizing the acid.

10. The method of claim 1, wherein removing the alcohol comprises evaporating the alcohol.

11. The method of claim 1, wherein the acid is sulfuric acid, triflic acid, hydrochloric acid, hydrobromic acid, hydroiodic acid, para-toluenesulfonic acid, or a combination thereof.

12. The method of claim 1, wherein the fatty acids of the crosslinked polymer comprise 16-hydroxyhexadecanoic acid, 9,16-dihydroxyhexadecanoic acid, 10,16-dihydroxyhexadecanoic acid, 18-hydroxyoctadecanoic acid, 18-hydroxy-(9Z)-octadec-9-enoic acid, 9,10-epoxy-18-hydroxyoctadecanoic acid, 9,10,18-trihydroxyoctadecanoic acid, or a combination thereof.

13. The method of claim 1, wherein the isolated fatty acid esters comprise ethyl 16-hydroxyhexadecanoate, ethyl 9,16-dihydroxyhexadecanoate, ethyl 10,16-dihydroxyhexadecanoate, ethyl 18-hydroxyoctadecanoate, ethyl 18-hydroxy-(9Z)-octadec-9-enoate, ethyl 9,10-epoxy-18-hydroxyoctadecanoate, ethyl 9,10,18-trihydroxyoctadecanoate, or a combination thereof.

14. The method of claim 1, where the composition is in the form of a solid powder.

15. The method of claim 14, wherein the powder has no substantial coloration.

16. A method of preparing a composition comprising cutin-derived monomeric or oligomeric esters, the method comprising:
    adding cutin to a solvent comprising an acid and an alcohol, wherein the acid is combined with the alcohol in superstoichiometric amounts;
    heating the solvent to a temperature from 78° C. to 120° C.;
    removing the solvent to form a mixture comprising the cutin-derived monomeric or oligomeric esters; and
    purifying the mixture to isolate the cutin-derived monomeric or oligomeric esters; wherein
    the cutin-derived monomeric or oligomeric esters comprise one or more compounds of Formula I:

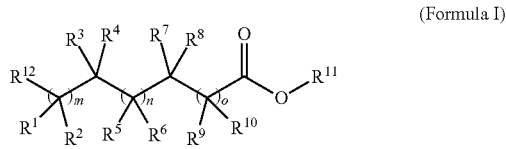

(Formula I)

wherein:
$R^1$, $R^2$, $R^3$, $R^4$, $R^5$, $R^6$, $R^7$, $R^8$, $R^9$, and $R^{10}$ are each independently —H, —$OR^{13}$, —$NR^{13}R^{14}$, —$SR^{13}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;
$R^{13}$ and $R^{14}$ are each independently —H, —$C_1$-$C_6$ alkyl, —$C_1$-$C_6$ alkenyl, or —$C_1$-$C_6$ alkynyl;
$R^{11}$ is -glyceryl, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;
$R^{12}$ is —OH, —H, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^{11}$; and
m, n, and o are each independently an integer in the range of 0 to 30, and $0 \leq m+n+o \leq 30$.

17. The method of claim 16, wherein the cutin contains endogenous water.

18. The method of claim 17, wherein the method is characterized as only requiring a single step to obtain the mixture comprising the cutin-derived monomeric or oligomeric esters from the cutin.

19. The method of claim 16, wherein the alcohol comprises ethanol, methanol, propanol, glycerol, or isopropanol.

20. The method of claim 16, where the composition is in the form of a solid powder.

21. The method of claim 20, wherein the powder has no substantial coloration.

22. A method of forming a protective coating on a substrate, comprising:
    obtaining fatty acid esters, the obtaining of the fatty acid esters comprising:
        treating a crosslinked polyester comprising polymerized mono- or polyhydroxy fatty acids with an acid and an alcohol at a temperature from 78° C. to 120°

C., wherein the acid is combined with the alcohol in superstoichiometric amounts;

removing the acid and the alcohol to form a mixture; and purifying the mixture to isolate the resulting fatty acid esters; and causing the fatty acid esters to be applied to a surface of the substrate to form the protective coating.

23. The method of claim 22, where the composition is in the form of a solid powder.

24. The method of claim 23, wherein the powder has no substantial coloration.

25. The method of claim 22, wherein the crosslinked polyester comprises cutin.

26. The method of claim 22, wherein the substrate is an edible substrate.

27. The method of claim 22, wherein the substrate comprises produce.

28. The method of claim 22, wherein the substrate comprises plant matter.

29. The method of claim 1, wherein crosslinked polyester is treated with the acid and the alcohol at a temperature from 100° C. to 120° C.

30. The method of claim 16, wherein the solvent is heated to a temperature from 100° C. to 120° C.

* * * * *